US011419488B2

(12) United States Patent
Otani

(10) Patent No.: US 11,419,488 B2
(45) Date of Patent: Aug. 23, 2022

(54) ENDOSCOPE SYSTEM

(71) Applicant: FUJIFILM Corporation, Tokyo (JP)

(72) Inventor: Kenichi Otani, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 380 days.

(21) Appl. No.: 16/509,504

(22) Filed: Jul. 12, 2019

(65) Prior Publication Data

US 2020/0069163 A1    Mar. 5, 2020

(30) Foreign Application Priority Data

Sep. 5, 2018  (JP) .............................. JP2018-165806

(51) Int. Cl.
*A61B 1/00* (2006.01)
*A61B 1/06* (2006.01)
(Continued)

(52) U.S. Cl.
CPC .............. *A61B 1/0638* (2013.01); *A61B 1/04* (2013.01); *A61B 1/0676* (2013.01);
(Continued)

(58) Field of Classification Search
CPC ....... A61B 1/0638; A61B 1/04; A61B 1/0676; A61B 1/00009; A61B 1/0684; A61B 5/1459; A61B 1/00006; A61B 1/0669; A61B 1/063; A61B 1/0653; A61B 1/0005; G02B 23/2461; H04N 5/2354; H04N 9/04511; H04N 5/2351; H04N 2005/2255
(Continued)

(56) References Cited

U.S. PATENT DOCUMENTS 8,535,221 B2   9/2013 Saito
9,526,408 B2   12/2016 Yamaguchi et al.
(Continued)

FOREIGN PATENT DOCUMENTS

EP   3011892   4/2016
EP   3231352   10/2017
(Continued)

OTHER PUBLICATIONS

"Office Action of Japan Counterpart Application", dated Apr. 13, 2021, with English translation thereof, p. 1-p. 13.
(Continued)

*Primary Examiner* — Timothy J Neal
*Assistant Examiner* — Sung Ham
(74) *Attorney, Agent, or Firm* — JCIPRNET

(57) ABSTRACT

An endoscope system includes a plurality of light sources which emits light having different wavelengths, a photodetector which is provided in each of the plurality of light sources, and which receives a part of the light of the plurality of light sources and obtains information on a light emitting quantity of the plurality of light sources, an image acquisition unit that acquires an image to be observed for each illumination light using at least first illumination light and second illumination light, composed of the light emitted from at least one of the plurality of light sources, and a control unit that makes a mutual image signal ratio constant in the plurality of images acquired by the image acquisition unit.

18 Claims, 12 Drawing Sheets

(51) Int. Cl.
*A61B 1/04* (2006.01)
*G02B 23/24* (2006.01)

(52) U.S. Cl.
CPC ...... *G02B 23/2461* (2013.01); *A61B 1/00009* (2013.01); *A61B 1/0684* (2013.01)

(58) Field of Classification Search
USPC .......................... 348/45, 70; 362/84; 600/109
See application file for complete search history.

(56) References Cited

U.S. PATENT DOCUMENTS

| | | | | |
|---|---|---|---|---|
| 2011/0237885 | A1* | 9/2011 | Matsubara | A61B 1/063 600/109 |
| 2016/0037999 | A1* | 2/2016 | Yabe | A61B 1/045 600/109 |
| 2016/0223807 | A1* | 8/2016 | Otani | A61B 1/0638 |
| 2016/0306163 | A1* | 10/2016 | Sakai | A61B 1/0638 |
| 2017/0272720 | A1* | 9/2017 | Oki | H04N 9/73 |
| 2018/0330659 | A1* | 11/2018 | Oki | G09G 3/22 |
| 2019/0068864 | A1 | 2/2019 | Ohashi et al. | |
| 2019/0110671 | A1* | 4/2019 | Daidoji | A61B 1/06 |
| 2020/0154028 | A1* | 5/2020 | Muramatsu | H04N 9/07 |
| 2021/0113058 | A1* | 4/2021 | Yamazaki | A61B 1/00006 |
| 2021/0120646 | A1* | 4/2021 | Oki | H05B 47/10 |

FOREIGN PATENT DOCUMENTS

| | | |
|---|---|---|
| JP | 2012066066 | 4/2012 |
| JP | 2012110485 | 6/2012 |
| JP | 2012228503 | 11/2012 |
| JP | 2014124772 | 7/2014 |
| JP | 2018000228 | 1/2018 |
| JP | 2018033719 | 3/2018 |

OTHER PUBLICATIONS

"Search Report of Europe Counterpart Application", dated Jan. 29, 2020, p. 1-p. 8.
"Office Action of Europe Counterpart Application", dated Oct. 21, 2020, p. 1-p. 5.

* cited by examiner

ENDOSCOPE SYSTEM

CROSS-REFERENCE TO RELATED APPLICATIONS

The present application claims priority under 35 U.S.C. § 119 to Japanese Patent Application No. 2018-165806, filed on Sep. 5, 2018. Each of the above application(s) is hereby expressly incorporated by reference, in its entirety, into the present application.

BACKGROUND OF THE INVENTION

1. Field of the Invention

The present invention relates to an endoscope system that acquires an endoscopic image to be observed using a plurality of light sources having different wavelengths, and particularly to an endoscope system that acquires an image to be observed for each illumination light and makes a mutual image signal ratio constant in a plurality of images by completely turning off and turning on the illumination light.

2. Description of the Related Art

In recent medical care, diagnosis using an endoscope system comprising a light source device for endoscopes, an electronic endoscope (endoscope), a processor device, and the like is widely performed. The light source device for endoscopes generates illumination light to irradiate an observation object. The electronic endoscope captures the observation object irradiated with the illumination light with an image sensor to generate image signals. The processor device performs image processing of the image signals generated by the electronic endoscope to generate an observation image for display on a monitor.

In the related art, in the light source device for endoscopes, lamp light source, such as a xenon lamp and a halogen lamp, which emit white light as the illumination light, are used. However, in recent years, instead of the lamp light source, a semiconductor light source such as a laser diode (LD) that emits light of a specific color or a light emitting diode (LED), is used. It is effective to use the above-described semiconductor light source also in terms of energy conservation, life elongation, and installation of a narrow band imaging function.

Further, in the endoscope system, various observation methods have been proposed for the observation object. For example, there are two types of observation modes of single-frame observation mode and multi-frame observation mode. In the single-frame observation mode, an observation image is generated using one or more captured images obtained in an imaging frame. In the multi-frame observation mode, one observation image is generated using a plurality of captured images obtained in a plurality of imaging frames.

There is an endoscope system disclosed in JP2018-033719A as an endoscope system which can carry out the multi-frame observation mode, for example.

The endoscope system disclosed in JP2018-033719A comprises a light source unit that generates illumination light, an image sensor that images an observation object using the illumination light in units of the imaging frame consisting of a readout period during which a signal is read out from a pixel and an accumulation period that is a maximum period during which an electric charge can accumulated to the pixel, a light source control unit that changes wavelength range of the illumination light or spectral spectrum for each imaging frame, an image processing unit that generates one observation image using a plurality of captured images acquired in the plurality of imaging frames having different wavelength ranges of the illumination light or the spectral spectrums, an imaging control unit that extends or shortens length of the accumulation period or the readout period of each imaging frame in a constant total time while making the total time of the accumulation period and the readout period of the plurality of imaging frames for obtaining the plurality of captured images used for generation of the observation image constant.

Further, JP2012-110485A discloses a light source device comprising n number of first semiconductor light sources (n is an integer of equal to or more than 2) that emit light in the same wavelength range, and light source control means for controlling the first semiconductor light sources. The light source control means considers a value between a maximum light emitting quantity of the first light obtained in a case where light is emitted from the m number of first semiconductor light sources (m is an integer of $1 \leq m \leq n-1$) and a minimum light emitting quantity of second light obtained in a case where light is emitted from the (m+1) number of first semiconductor light sources, as a reference light emitting quantity, and turns on the (m+1) number of first semiconductor light sources in a case where a target light emitting quantity of light to be output from the light source device is larger than the reference light emitting quantity such that the light emitting quantity of the second light meets the target light emitting quantity, and turns on the m number of first semiconductor light sources in a case where the target light emitting quantity is smaller than the reference light emitting quantity such that the light emitting quantity of the first light meets the target light emitting quantity.

JP2012-110485A describes that the light emitting quantity of violet laser light overshoots in predetermined time right after changed from normal light observation to special light observation. It is described to control a violet laser light source not to be completely turned off to reduce an overshoot of the light emitting quantity of the violet laser light.

SUMMARY OF THE INVENTION

As one using the multi-frame observation mode indicated in the endoscope system disclosed in JP2018-033719A, for example, there is oxygen saturation imaging.

The oxygen saturation imaging switches the illumination wavelength and acquires the plurality of images and thus, a single image related to tissue oxygen saturation is generated. That is, the multi-frame image processing is performed. While a normal endoscopic illumination is continuously turned on during observation, it is necessary for each illumination light to be completely turned off and turned on in short time in synchronization with imaging frame in the oxygen saturation imaging.

When the light source is converted from turning off state to turning on state in order to obtain one image, response delay or overshoot of the semiconductor light source occurs. In a case where a ratio relationship between a light emitting quantity of a first frame and a light emitting quantity of a second frame deviates from a predetermined range due to the above-described overshoot or response delay, the ratio of two image signals also changes and thus, the oxygen saturation cannot be accurately calculated. Particularly, in an observation function for imaging a quantitative index such as oxygen saturation, the illumination light is completely turned off and turned on in a short time, and the overshoot and the response delay occur to cause an error influence which is larger than the conventional white light observation and image-emphasized observation and thus, high-precision control is required. However, sufficient countermeasures have not been prepared.

Further, as in JP2012-110485A, in a case where a violet laser light source is controlled not to be completely turned off in order to reduce the overshoot, it is not effective countermeasure to perform numerical measurement such as the above-described oxygen saturation imaging because in a case where unnecessary light is present, measurement accuracy declines. In addition, in a case where the image sensor is a Complementary Metal Oxide Semiconductor (CMOS) sensor, color mixing may occur and thus, the measurement accuracy may decline.

Also, as described above, the semiconductor light source is used in the endoscope system. However, the semiconductor light source causes the overshoot of the light emitting quantity or the response delay at the time of turning on the light, due to light emitting response characteristics of the semiconductor light source. In addition, in recent years, the output of the semiconductor light source has been increasing, and a high-output light source has been used in an endoscope light source, a projector, and the like, in order to increase the brightness.

Although a control circuit also needs to correspond to an increased driving current, generally it is difficult to simultaneously achieve high output of the driving circuit and high speed response. Therefore, the driving circuit of the high-output semiconductor light source may cause the response delay of the light source.

Also, the semiconductor light source is often controlled by a switching regulator circuit, and in a case where a switching frequency is increased, load response is improved. However, because power efficiency deteriorates and high heat is generated, it is difficult to achieve high output.

An object of the present invention is to solve problems in the above-described related art, and to provide an endoscope system that acquires images to be observed for each illumination light by completely turning off and turning on the illumination light and makes a mutual image signal ratio in the plurality of images constant.

In order to achieve the above-described object, the invention provides an endoscope system comprising a plurality of light sources which emits light having different wavelengths, a photodetector which is provided in each of the plurality of light sources, and which receives a part of light from the plurality of light sources and obtains information on a light emitting quantity of the plurality of light sources, an image acquisition unit which acquires an image to be observed for each illumination light using at least first illumination light and second illumination light composed of light emitted from at least one of the plurality of light sources, and a control unit which makes a mutual image signal ratio constant in the plurality of images acquired by the image acquisition unit.

It is preferable that the first illumination light and the second illumination light be emitted from different light sources.

It is preferable that the first illumination light and the second illumination light be emitted from the same light source.

It is preferable that the control unit include a light source control unit that changes a light emitting quantity of the light source according to a light receiving quantity of the photodetector such that the light emitting quantity of the light source meets a target light quantity, the endoscope system further comprise a measurement unit that obtains an integrated light quantity obtained using the photodetector in a predetermined error calculation period after turning on the light source, and an error calculation unit that obtains a difference between the integrated light quantity obtained by the measurement unit and the target light quantity, and the control unit change the target light quantity after the error calculation period according to the difference obtained by the error calculation unit to make an integral light quantity constant in a predetermined exposure period.

It is preferable that the endoscope system further comprise a measurement unit that obtains an integrated light quantity obtained using the photodetector in a predetermined error calculation period after turning on the light source, and an error calculation unit that obtains a difference between the integrated light quantity obtained by the measurement unit and a target light quantity, in which the control unit changes a predetermined exposure period according to the difference obtained by the error calculation unit to make an integral light quantity constant in the exposure period.

It is preferable that the endoscope system further comprise a measurement unit that obtains an integrated light quantity obtained using the photodetector in a predetermined error calculation period after turning on the light source, and an error calculation unit that obtains a difference between the integrated light quantity obtained by the measurement unit and a target light quantity, in which the control unit changes a timing of turning off the light source after the error calculation period according to the difference obtained by the error calculation unit to make an integral light quantity constant in a predetermined exposure period.

It is preferable that the control unit include a light source control unit that changes a light emitting quantity of the light source according to a light receiving quantity of the photodetector such that the light emitting quantity of the light source meets a target light quantity, the endoscope system further comprise a measurement unit that obtains an integrated light quantity obtained using the photodetector in a predetermined error calculation period after turning on the light source, and an error calculation unit that obtains a difference between the integrated light quantity obtained by the measurement unit and the target light quantity, and the control unit change the target light quantity of the second illumination light according to the difference obtained by the error calculation unit in the first illumination light to make a ratio of integrated light quantities constant in a predetermined exposure period in the plurality of images.

It is preferable that the endoscope system further comprise a measurement unit that obtains an integrated light quantity obtained using the photodetector in a predetermined error calculation period after turning on the light source, and an error calculation unit that obtains a difference between the integrated light quantity obtained by the measurement unit and a target light quantity, in which the control unit changes an exposure period of the second illumination light according to the difference obtained by the error calculation unit in the first illumination light to make a ratio of integrated light quantities constant in the exposure period in the plurality of images.

It is preferable that the endoscope system further include a measurement unit that obtains an integrated light quantity obtained using the photodetector in a predetermined error calculation period after turning on the light source, and an error calculation unit that obtains a difference between the integrated light quantity obtained by the measurement unit and a target light quantity, in which the control unit changes a timing of turning off the second illumination light according to the difference obtained by the error calculation unit in the first illumination light to make a ratio of integrated light quantities constant in a predetermined exposure period in the plurality of images.

It is preferable that the plurality of light sources have a laser diode or a light emitting diode.

It is preferable that the photodetector be a photodiode.

According to the present invention, it is possible to provide an endoscope system that acquires images to be observed for each illumination light by completely turning off and turning on the illumination light and makes a mutual image signal ratio in a plurality of images constant.

DESCRIPTION OF THE PREFERRED EMBODIMENTS

Hereinafter, an endoscope system according to an embodiment of the invention will be described in detail on the basis of the preferable embodiment illustrated in attached drawings.

In addition, the drawings to be described below are illustrative drawings for describing the invention, and the invention is not limited to the following drawings.

In addition, in the following, "to" showing a numerical range includes numerical values described on both sides thereof. For example, "$\varepsilon$ is a numerical value $\alpha$ to a numerical value $\beta$" means that a range of $\varepsilon$ is a range including the numerical value $\alpha$ and the numerical value $\beta$, and in a case where these are expressed by mathematical symbols, the formula would be $\alpha \leq \varepsilon \leq \beta$.

"Parallel" or the like include error ranges that are generally allowed in a corresponding technical field unless otherwise specified. Additionally the "same" includes error ranges that are generally allowed in a corresponding technical field.

Endoscope System

Generally, a wavelength of blue light is about 445 nm to about 485 nm. For example, a color between blue and green is referred to as bluish green and may be distinguished from blue. However, in an endoscope system 10, there is no need for excessively subdividing the type of color (the name of color) regarding at least light components emitted by individual light sources of the light source unit. For this reason, a color of light having a wavelength of about 440 nm or more and less than about 490 nm is referred to as blue. Additionally, a color of light having a wavelength of about 490 nm or more and less than about 600 nm is referred to as green, and a color of light having a wavelength of about 600 nm or more and less than about 680 nm is referred to as red. Also, a color of visible light having a wavelength of less than "about 440 nm" that is a lower limit of the wavelength of the above-described blue light, for example, the color of visible light having a wavelength of about 380 nm or more and less than about 440 nm is referred to as violet light, and a color of light which has a wavelength shorter than violet but for which an image sensor 48 has sensitivity is referred to as ultraviolet. Additionally, red light which has a wavelength of "about 680 nm" or more that is an upper limit of the wavelength of the above-described red light and for which the image sensor 48 has sensitivity is referred to as infrared. Additionally, the term "broadband" means that a wavelength range reaches the wavelength range of a plurality of colors. White means a color of light including at least the light that belongs to the above-described blue or violet, the light that belongs to green, or the light that belongs to red.

Hereinafter, the endoscope system will be described in more detail.

Figure 1:
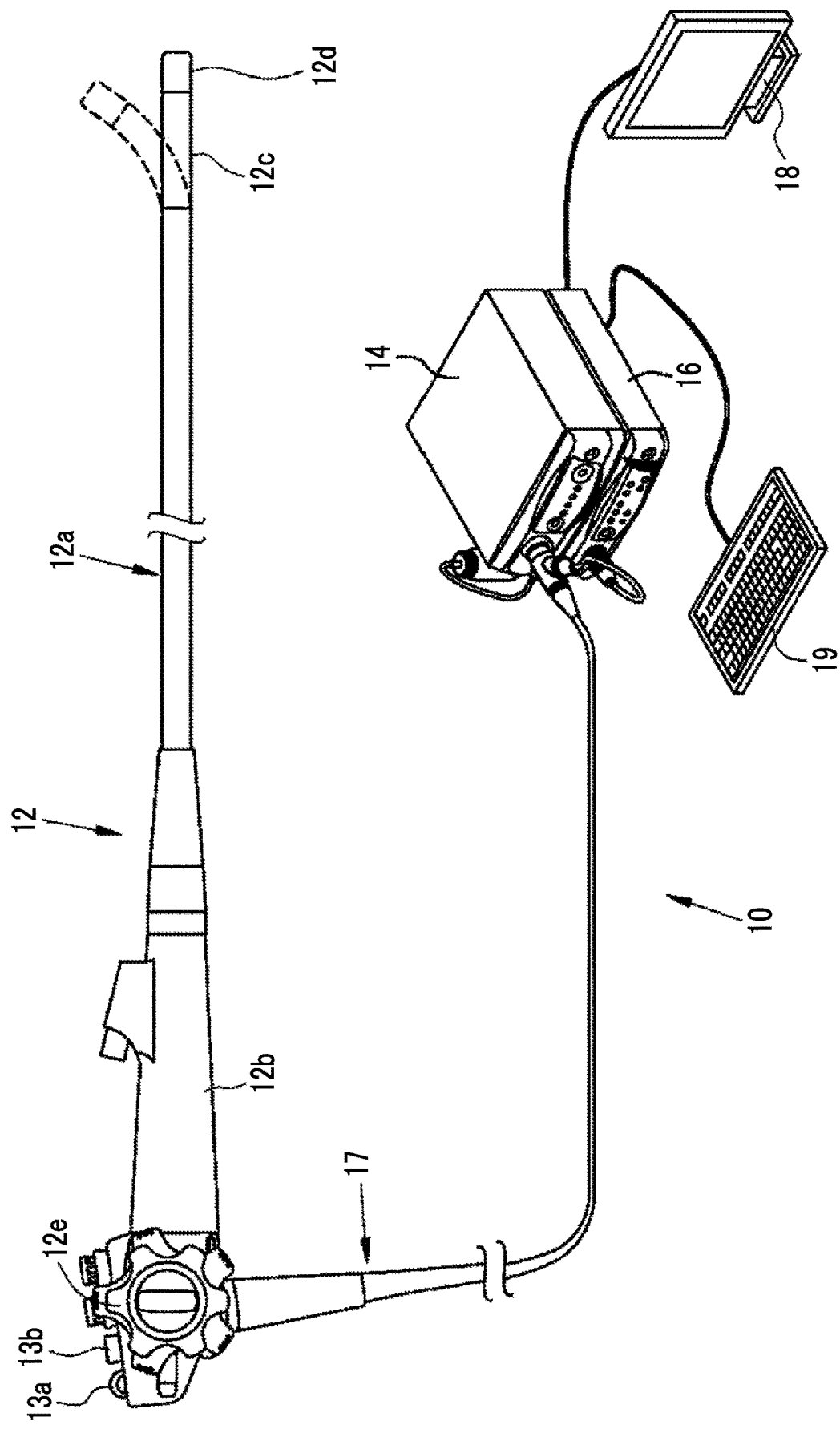
FIG. 1 is a perspective view conceptually illustrating an example of an endoscope system of an embodiment of the invention.
Figure 2:
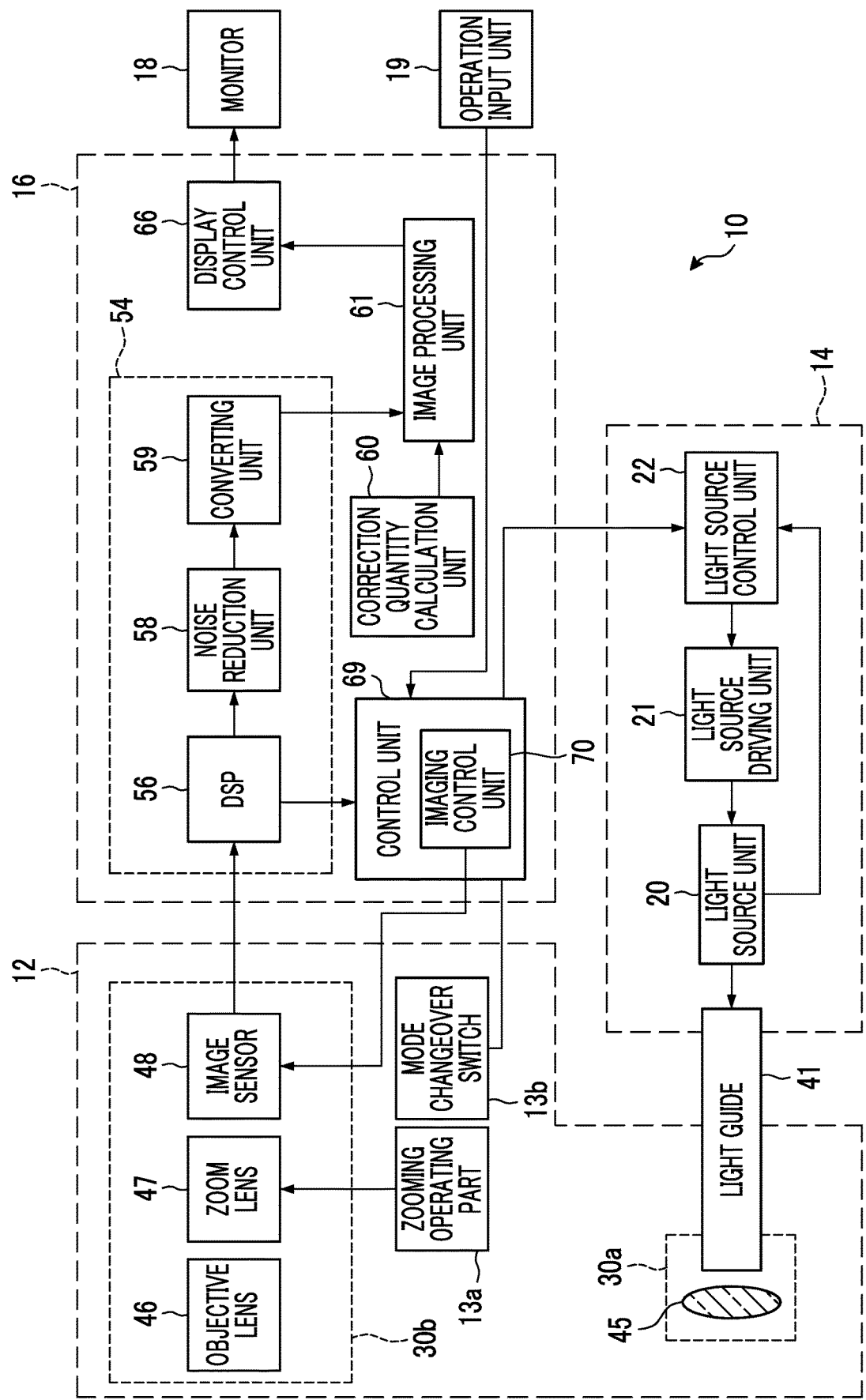
FIG. 2 is a block diagram conceptually illustrating the example of the endoscope system of the embodiment of the invention.

FIG. 1 is a perspective view conceptually illustrating an example of the endoscope system of the embodiment of the invention, and FIG. 2 is a block diagram conceptually illustrating an example of the endoscope system of the embodiment of the invention.

As illustrated in FIG. 1, the endoscope system 10 comprises a scope of endoscope (hereinafter simply referred to as an endoscope) 12 that images an observation region within a living body (within a subject) that is an observation object, a processor device 16 that generates a display image of a region to be observed on the basis of image signals obtained by the imaging, a light source device 14 for endoscopes (hereinafter simply referred to as a light source device) that supplies illumination light, with which the observation region is irradiated, to the endoscope 12, and a monitor 18 that displays the display image. A console 19, which is operation input unit, such as a keyboard and a mouse, is connected to the processor device 16.

The endoscope system 10 has, for example, two types of observation mode of single-frame observation mode and multi-frame observation mode. In the single-frame observation mode, an observation image is generated using one or more captured images obtained from an imaging frame. The single-frame observation mode corresponds to a normal observation mode to be described below.

In the multi-frame observation mode, one observation image is generated using a plurality of captured images obtained from a plurality of imaging frames. A blood vessel emphasis observation mode to be described below corresponds to the multi-frame observation mode.

Additionally, the endoscope system 10 is capable of executing the normal observation mode for observing the observation region, and the blood vessel emphasis observation mode for enhancing and observing blood vessels that are present inside a mucous membrane of the observation region. In addition, the endoscope system 10 has an oxygen saturation observation mode for calculating oxygen saturation of the observation object, and generating and displaying an observation image (hereinafter referred to as an oxygen saturation image) representing the calculated oxygen saturation.

The blood vessel emphasis observation mode is a mode for visualizing a pattern of the blood vessels as blood vessel information and performing diagnosis, such as differentiation of a malignant or benign tumor. In this blood vessel emphasis observation mode, the observation region is irradiated with illumination light including many components of light having a specific wavelength range in which the absorbance for hemoglobin in blood is high.

In the normal observation mode, a normal observation image suitable for observation of the entire observation region is generated as the display image. In the blood vessel emphasis observation mode, a blood vessel emphasis observation image suitable for observation of the pattern of the blood vessels is generated as the display image.

The endoscope 12 has an insertion part 12a to be inserted into the subject, an operating part 12b provided at a proximal end portion of the insertion part 12a, a bending part 12c provided on a distal end side of the insertion part 12a, and a distal end part 12d. By operating an angle knob 12e of the operating part 12b, the bending part 12c is bent. The distal end part 12d is directed in a desired direction as a result of the bending of the bending part 12c. In addition, the distal end part 12d is provided with a jet port (not illustrated) that jets air, water, or the like toward the observation object. Additionally, the operating part 12b is provided with a forceps port for inserting a treatment tool, an air/water supply button that is operated in a case where performing air supply or water supply from an air/water supply nozzle, a freeze button (not illustrated) for capturing a still image, a zooming operating part 13a, and a mode changeover switch 13b in addition to the angle knob 12e. The zooming operating part 13a is used for imaging the observation object in an enlarged or reduced manner. The mode changeover switch 13b is used for switching a plurality of observation modes in a case where the endoscope system 10 has the plurality of observation modes.

Additionally, the endoscope 12 comprises a universal cord 17 for connecting the endoscope 12 to the processor device 16 and the light source device 14.

A communication cable or light guide 41 (refer to FIG. 2) extended from the insertion part 12a is inserted through the universal cord 17, and a connector is attached to one end on the side of the processor device 16 and the light source device 14. The connector is a composite connector including a communication connector and a light source connector. The communication connector and the light source connector are attachably and detachably connected to the processor device 16 and the light source device 14, respectively. One end of the communication cable is disposed at the communication connector. An incident end of the light guide 41 is disposed at the light source connector.

As illustrated in FIG. 2, the light source device 14 comprises a light source unit 20 having two or more of light sources having different dominant wavelengths, a light source control unit 22 that controls the light emitting timing of the light source unit 20, the light emitting quantity, and the like, and a light source driving unit 21 that generates a driving current according to a control signal of the light source control unit 22 and supplies the driving current (driving signal) to each light source to make the light source emit light.

In the light source device 14, the light source control unit 22 controls the light source driving unit 21 such that illumination light Ls (refer to FIG. 5) is radiated from the light source unit 20 to an object Ob (refer to FIG. 5) that is the observation object with a specific quantity of light. For example, even in a case where a distance Ld (refer to FIG. 5) of a distal end part 12d (refer to FIG. 5) of the endoscope and the object Ob (refer to FIG. 5) changes, the quantity of the illumination light Ls is controlled such that the brightness of an endoscopic image becomes constant. In this case, the quantity of the illumination light Ls is controlled such that the brightness value becomes constant, for example, using the brightness value obtained from a sensor signal of the image sensor 48.

In this case, the light source unit 20 is provided with photodetectors 91, 92, and 93 (refer to FIG. 5) as will be described below, and information on the quantities of light of the individual light sources detected by the photodetectors 91, 92, and 93 (refer to FIG. 5) is input to the light source control unit 22, and the information on the quantities of light of the individual light sources is obtained. The light emitting quantities of the light sources of the light source unit 20 are accurately and automatically controlled on the basis of the information on the quantities of light of the individual light sources and the brightness value of the image sensor 48.

The illumination light emitted from the light source unit 20 is incident on the light guide 41. The light guide 41 is built within the endoscope 12 and the universal cord 17 and propagates the illumination light up to the distal end part 12d of the endoscope 12. The universal cord 17 is a cord that connects the endoscope 12, and the light source device 14 and the processor device 16 together.

The distal end part 12d of the endoscope 12 is provided with an illumination optical system 30a and an imaging optical system 30b. The illumination optical system 30a has an illumination lens 45, and the illumination light is radiated to the observation object via the illumination lens 45. The imaging optical system 30b has an objective lens 46, a zoom lens 47, and an image sensor 48. The image sensor 48 images the observation object using reflected light or the like of the illumination light returning from the observation object via the objective lens 46 and the zoom lens 47.

Scattered light, fluorescence emitted from the observation object, fluorescence resulting from a medicine administered to the observation object, in addition to the reflected light, or the like is included in the above-described reflected light or the like of the illumination light returning from the observation object.

In addition, the zoom lens 47 is moved by operating the zooming operating part 13a. As a result, the observation object is imaged using the image sensor 48 in an enlarged or reduced manner to be observed.

In the image sensor 48, for example, photoelectric conversion elements, which are used in a charge coupled device (CCD) sensor, a complementary metal oxide semiconductor (CMOS) sensor, or the like are used. In the image sensor 48 using a photoelectric conversion element, received light is photoelectrically converted, and an electric charge of a signal according to the light receiving quantity is accumulated as a sensor signal for each pixel. The electric charge of a signal for each pixel is converted into a voltage signal and is read from the image sensor 48. The voltage signal for each pixel read from the image sensor 48 is input to a digital signal processor (DSP) 56 as an image signal.

The image sensor 48 performs, for example, an accumulation operation in which the electric charge of a signal is accumulated in a pixel, and a reading operation in which the accumulated electric charge of a signal is read out, within an acquisition period of one frame. The light source device 14 generates the illumination light in conformity with the timing of the accumulation operation of the image sensor 48, and make the illumination light incident on the light guide 41.

Figure 3:
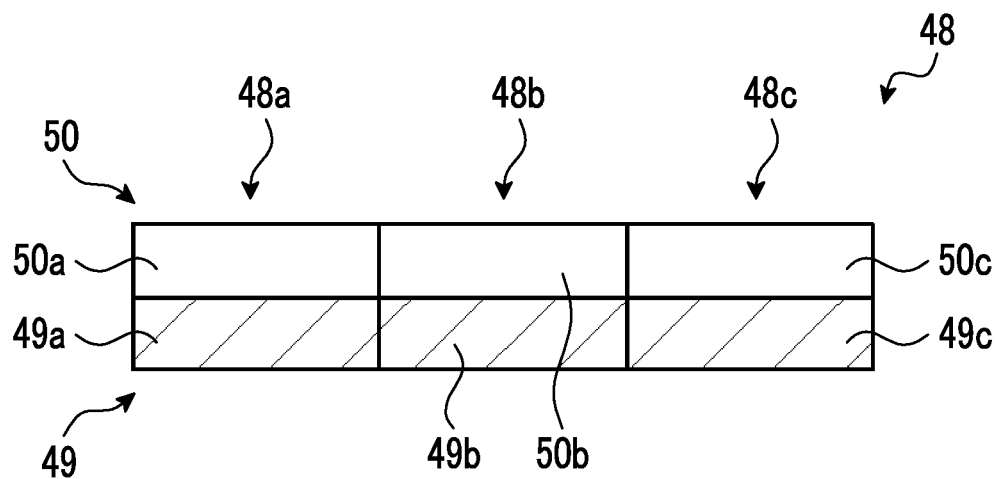
FIG. 3 is a schematic view illustrating an example of an image sensor of the endoscope system of the embodiment of the invention.

As illustrated in FIG. 3, the image sensor 48 has a pixel unit 49 having a photoelectric conversion function, and a filter unit 50 having the spectral transmission characteristics for a specific wavelength range. A first element part 48a, a second element part 48b, and a third element part 48c are composed of the pixel unit 49 and the filter unit 50. The electric charge of a signal is accumulated as a sensor signal as described above in the pixel unit 49 having the photoelectric conversion function. The image sensor 48 also has an electronic shutter (not illustrated).

In the image sensor 48, the first element part 48a has a first pixel 49a having the photoelectric conversion function, and a first filter 50a having the spectral transmission characteristics for a first color component. A first signal value of the first color component is obtained in the first element part 48a according to the light incident on the image sensor 48.

The second element part 48b has a second pixel 49b having the photoelectric conversion function, and a second filter 50b having the spectral transmission characteristics for a second color component. A second signal value of the second color component is obtained in the second element part 48b according to the light incident on the image sensor 48.

The third element part 48c has a third pixel 49c having the photoelectric conversion function, and a third filter 50c having the spectral transmission characteristics for a third color component. The third color component is a color other than the first color component and the second color component. A third signal value of the third color component is obtained in the third element part 48c according to the light incident on the image sensor 48.

The image sensor 48 has, for example, a color sensor of a primary color system having a color filter in each pixel. The first filter 50a, the second filter 50b, and the third filter 50c are composed of, for example, color filters. In this case, the first filter 50a, the second filter 50b, and the third filter 50c of the image sensor 48 are, for example, any one of a red color filter (R color filter), a green color filter (G color filter), or blue color filter (B color filter). The first element part 48a, the second element part 48b and the third element part 48c are appropriately determined according to the above-described first color component, second color component, and third color component.

Among the individual pixels of the first pixel 49a, the second pixel 49b, and the third pixel 49c, a pixel having the R color filter is an R pixel, a pixel having the G color filter is a G pixel, and a pixel having the B color filter is a B pixel. As sensor signals of the image sensor 48, an R signal is obtained from the R pixel, a G signal is obtained from the G pixel, and a B signal is obtained from the B pixel. The R signal, the G signal, and the B signal are input to the DSP 56 as image signals.

In this way, since the image sensor 48 has, for example, three-color pixels of the R pixel, the G pixel, and the B pixel, an R image obtained by imaging the observation object with the R pixel, a G image obtained by imaging the observation object with the G pixel, and a B image obtained by imaging the observation object with the B pixel are simultaneously obtained in a case where the observation object is imaged using white light for the illumination light.

Making a mutual image signal ratio in the plurality of images constant means that the ratio of the R pixel value, the G pixel value, and the B pixel value of each image is the same as one another. In a case where the above-described ratio is the same, each image can be quantified and digitized based on the image data of each image.

For example, the accuracy can be increased in the case of obtaining oxygen saturation, blood volume, and the like.

In addition, in a case where the above-described ratio is the same, even if the brightness of the image is different, a tone, and the like do not change and is the same as the observation image. Therefore, excellent image quality can be obtained even in the normal-observation mode.

Figure 4:
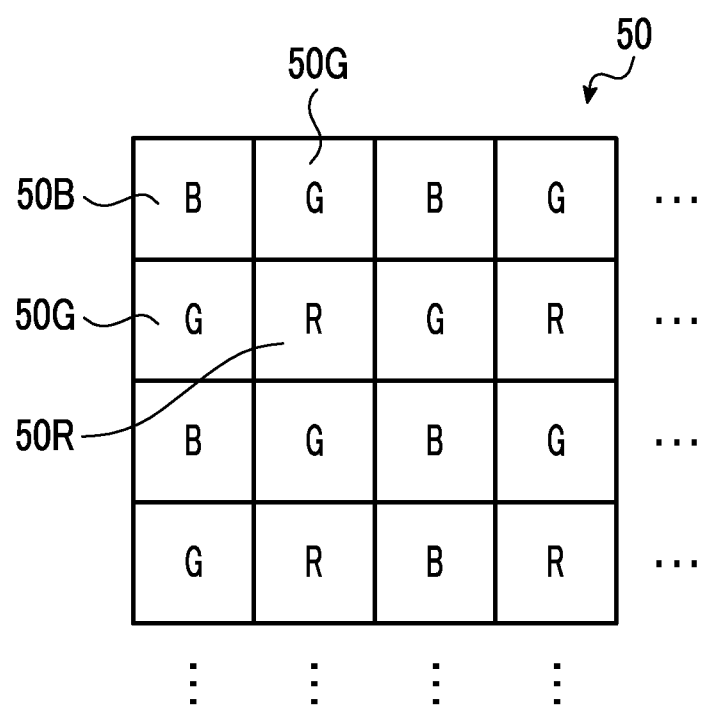
FIG. 4 is a schematic view illustrating an example of an arrangement of color filters of the image sensor of the endoscope system of the embodiment of the invention.

Although an arrangement of an R color filter 50R (refer to FIG. 4), a G color filter 50G (refer to FIG. 4), and a B color filter 50B (refer to FIG. 4) is not particularly limited, these color filters are disposed in a ratio of R:G:B=1:2:1 in consideration of visibility, for example, as illustrated in FIG. 4.

In addition, for example, a signal value of the R signal is equivalent to a second signal value, a signal value of the G signal is equivalent to a first signal value, and a signal value of the B signal is equivalent to a third signal value.

In addition, although the color sensor of the primary color system has been exemplified as the image sensor 48, the image sensor is not limited thereto, and a color sensor of a complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the above-described individual color pixels in a case where the color sensor of the complementary color system is used can be converted into the B image, the G image, and the R image in a case where color conversion of complementary color and primary color is performed. Additionally, instead of the color sensor, a monochrome sensor that is not provided with the color filters can be used as the image sensor 48. In this case, the above-described individual images can be obtained by sequentially imaging the observation object using illumination light components of individual colors, such as BGR.

Additionally, a communication cable that performs communication of the driving signal for driving the image sensor 48 and the image signals output from the image sensor 48, and the light guide 41 that guides the illumination light supplied from the light source device 14 to an illumination window are inserted through the insertion part 12a illustrated in FIG. 1.

As illustrated in FIG. 2, the processor device 16 has an image acquisition unit 54, a correction quantity calculation unit 60, an image processing unit 61, a display control unit 66, and a control unit 69. The processor device 16 is equivalent to a processor of the invention.

The image acquisition unit 54 obtains the image signals from the individual pixels of the image sensor 48 and acquires captured images of a plurality of colors, which are obtained by imaging the observation object using the image sensor 48. Specifically, the image acquisition unit 54 acquires a set of the B image, the G image, and the R image for each imaging frame. Additionally, the image acquisition unit 54 has the DSP 56, a noise reduction unit 58, and a converting unit 59, and performs various kinds of processing on the acquired captured images using these units. For example, the R signal, the G signal, and the B signal obtained as the sensor signals from the individual pixels of the image sensor 48 are output to the correction quantity calculation unit 60 and the control unit 69.

The DSP 56 performs various kinds of processing, such as defect correction processing, offset processing, gain correction processing, linear matrix processing, gamma conversion processing, demosaicing processing, and YC conversion processing, on the acquired captured images, as needed. Additionally, in the DSP 56, the brightness value is obtained from the sensor signal of the image sensor 48 input as the image signal. In addition, for example, the G signal may be used as the brightness value.

The defect correction processing is a processing of correcting a pixel value of a pixel corresponding to a defective pixel of the image sensor 48.

The offset processing is a processing of reducing a dark current component from the images subjected to the defect correction processing and setting an accurate zero level.

The gain correction processing is a processing of adjusting a signal level of each image by multiplying the images subjected to the offset processing by a gain.

The linear matrix processing is a processing of enhancing color reproducibility on the images subjected to the offset processing, and the gamma conversion processing is a processing of adjusting brightness or saturation of the image subjected to the linear matrix processing.

The demosaicing processing (also referred to as equalization processing or synchronization processing) is the processing of interpolating the pixel value of a missing pixel and is performed on the images subjected to the gamma conversion processing. The missing pixel is a pixel with no pixel value because pixels in other colors are disposed in the image sensor 48 due to the arrangement of color filters. For example, since the B image is an image obtained by imaging the observation object in the B pixel, there is no pixel value in pixels at positions corresponding to the G pixel and the R pixel of the image sensor 48. In the demosaicing processing, the pixel values of the pixels at the positions of the G pixel and the R pixel of the image sensor 48 are generated by interpolating the B image.

The YC conversion processing is a processing of converting the images subjected to the demosaicing processing into a brightness channel Y, a color difference channel Cb, and a color difference channel Cr.

The noise reduction unit 58 performs noise reduction processing using, for example, a moving average method, a median filter method, or the like, on the brightness channel Y, the color difference channel Cb, and the color difference channel Cr.

The converting unit 59 re-converts the brightness channel Y, the color difference channel Cb, and the color difference channel Cr after the noise reduction processing into images of respective colors of BGR.

The correction quantity calculation unit 60 performs correction for maintaining the tone of the endoscopic image, and calculates correction coefficient to be described below or stores the correction coefficient.

The image processing unit 61 performs color conversion processing, color emphasis processing, and structure emphasis processing on the B image, the G image, and the R image, equivalent to one imaging frame subjected to the above-described various kinds of processing to generate an observation image. In the color conversion processing, 3×3 matrix processing, grayscale conversion processing, three-dimensional look-up table (LUT) processing, or the like is performed on the images of the individual colors of BGR. The color emphasis processing is the processing of enhancing the colors of an image, and the structure emphasis processing is the processing of enhancing, for example, the tissue or structure of the observation object such as blood vessels and pit patterns.

The display control unit 66 sequentially acquires observation images from the image processing unit 61, converts the acquired observation images into a format suitable for display, and sequentially outputs and displays the converted images to and on the monitor 18. Accordingly, a doctor or the like can observe the observation object using still images or moving images of the observation images.

The control unit 69 has, for example, a central processing unit (CPU), and performs overall control of the endoscope system 10, such as emission timing of the illumination light and synchronous control of an imaging frame.

The control unit 69 comprises an imaging control unit 70 that controls the operation of the image sensor 48.

Additionally, in a case where the endoscope system 10 has the plurality of observation modes, the control unit 69 switches the illumination light via the light source control unit 22 by receiving an operation input from the mode changeover switch 13b. Accordingly, the observation mode is switched. The light source control unit 22 is included in the control unit 69.

In a case of the single-frame observation mode, the imaging control unit 70 controls the image sensor 48 so as to alternately repeat the accumulation period and the readout period at regular intervals, for example, every 1/60 second. Therefore, in the single-frame observation mode, the length of the imaging frame is constant.

The imaging control unit 70 adjusts a shutter speed of an electronic shutter (not illustrated) of the image sensor 48. For example, in a case of the multi-frame observation mode, a shutter speed of the electronic shutter changes.

The processor device 16 is electrically connected to the monitor 18 and the console 19. The monitor 18 outputs and displays the observation images, accompanying image information, and the like if necessary. The console 19 functions as a user interface that receives an input operation, such as function setting. In addition, an external recording unit (not illustrated) that records the images, the image information, and the like may be connected to the processor device 16.

Hereinafter, the configuration and the operation of the light source device 14 will be described in more detail. FIG.

5 is a schematic view illustrating a first example of the light source unit of the endoscope system of the embodiment of the invention.

Figure 5:
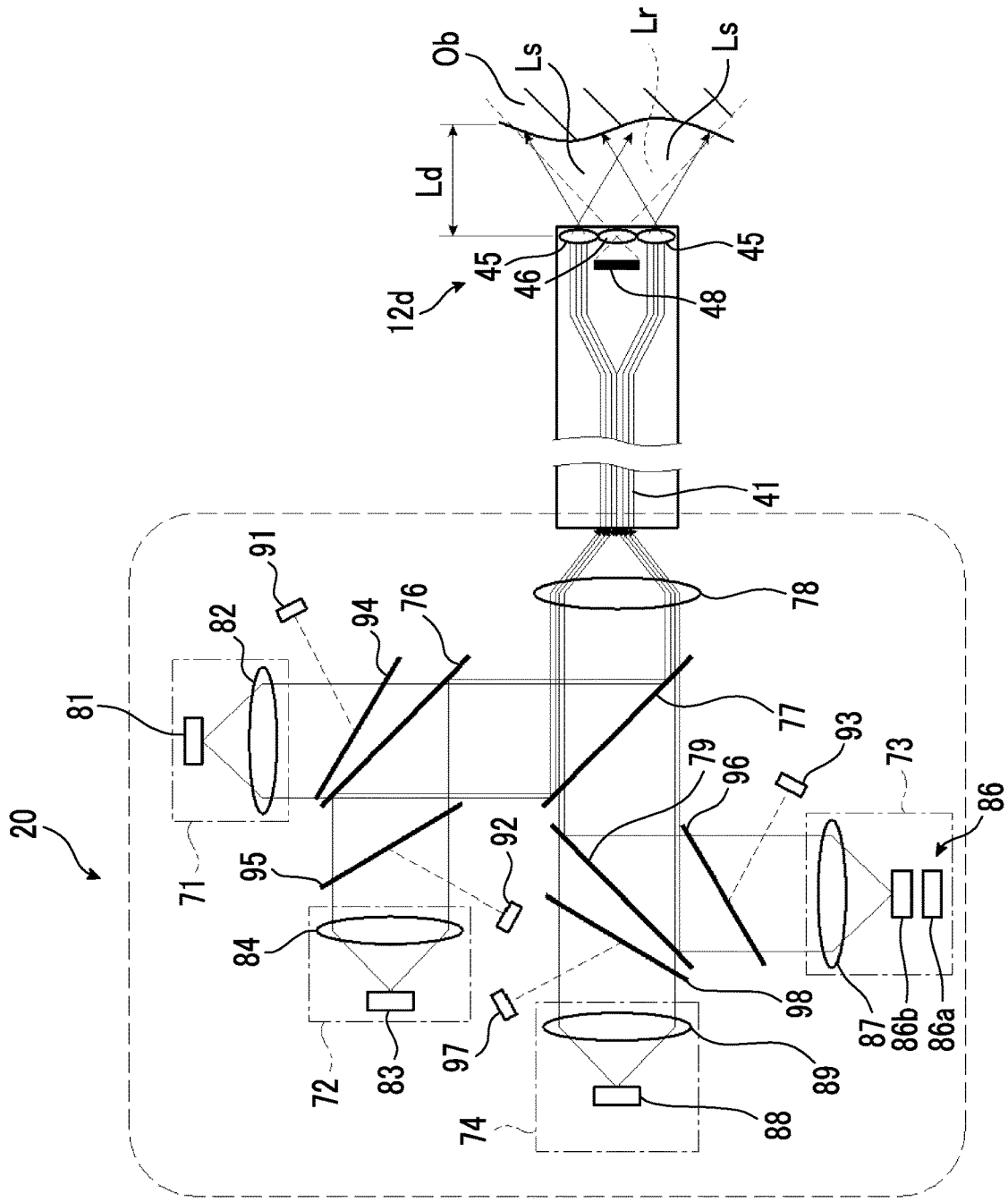
FIG. 5 is a schematic view illustrating a first example of a light source unit of the endoscope system of the embodiment of the invention.

The light source unit 20 of the light source device 14 illustrated in FIG. 5 has the plurality of light sources emitting light having different wavelengths, and has, for example, four light sources emitting light having different wavelengths.

The light source unit 20 has a first light source 71, a second light source 72, a third light source 73, and a fourth light source 74. The first light source 71, the second light source 72, the third light source 73, and the fourth light source 74 can independently control the light quantity, the timing of turning off the light, and the like. Additionally, the light source unit 20 comprises a cooling member, such as a heat sink, that cools light emitting element of individual light sources of the first light source 71, the second light source 72, the third light source 73, and the fourth light source 74.

In the light source device 14, the light emitted from the light source unit 20 passes through the light guide 41, and is radiated to the object Ob as the illumination light Ls. Reflected light Lr of the illumination light Ls radiated to the object Ob is incident on the image sensor 48 via the objective lens 46.

The first light emitted from the first light source 71 is incident on the light guide 41 via a multiplexing member 76 penetrating the first light, a multiplexing member 77 reflecting the first light, and a lens 78 in the light source unit 20. The lens 78 is disposed on the reflective surface side of multiplexing member 77. Moreover, the multiplexing member 76 and the multiplexing member 77 are spaced apart and disposed in parallel.

A beam splitter 94 is provided between the first light source 71 and the multiplexing member 76. A portion of the first light emitted by the first light source 71 is reflected in a predetermined ratio by the beam splitter 94. The light reflected by the beam splitter 94 is received by a photodetector 91. The light source control unit 22 has a function that automatically and accurately controls the first light emitting quantity of the first light source 71 using the quantity of the light detected by the photodetector 91.

The second light emitted by the second light source 72 is incident on the light guide 41 via the multiplexing member 76 and the multiplexing member 77, which reflect the second light, and the lens 78.

A beam splitter 95 is provided between the second light source 72 and the multiplexing member 76. A portion of the second light emitted by the second light source 72 is reflected in a predetermined ratio by the beam splitter 95. The light reflected by the beam splitter 95 is received by a photodetector 92. The light source control unit 22 has a function that automatically and accurately controls the light emitting quantity of the second light of the second light source 72 using the quantity of the light detected by the photodetector 92.

The third light emitted from the third light source 73 is incident on the light guide 41 via a multiplexing member 79 reflecting the third light, the multiplexing member 77 transmitting the third light and the lens 78. A multiplexing member 79 is provided between the fourth light source 74 and the multiplexing member 77.

A beam splitter 96 is provided between the third light source 73 and the multiplexing member 79. A portion of the third light emitted by the third light source 73 is reflected in a predetermined ratio by the beam splitter 96. The light reflected by the beam splitter 96 is received by a photodetector 93. The light source control unit 22 has a function that automatically and accurately controls the light emitting quantity of the third light of the third light source 73 using the quantity of the light detected by the photodetector 93.

The fourth light emitted from the fourth light source 74 is incident on the light guide 41 via the multiplexing member 79 and the multiplexing member 77 transmitting the fourth light, and the lens 78.

A beam splitter 98 is provided between the fourth light source 74 and the multiplexing member 79. A part of the fourth light emitted from the fourth light source 74 is reflected in a predetermined ratio by the beam splitter 98. The light reflected by the beam splitter 98 is received by a photodetector 97. The light source control unit 22 has a function that automatically and accurately controls the light emitting quantity of the fourth light of the fourth light source 74 using the light quantity detected by the photodetector 97.

The multiplexing member 76, the multiplexing member 77 and the multiplexing member 79 are, for example, dichroic mirrors, dichroic prisms, or the like. The lens 78 is for narrowing the light from the light source unit 20 to make the narrowed light incident on the light guide 41.

The photodetectors 91, 92, 93, and 97 are provided so as to acquire information on the light emitting quantity of each light source. Examples of the photodetectors 91, 92, 93, and 97 include photomultiplier tubes using a photoelectric effect, photoconductive elements, such as CdS or PbS, using electric resistance changes caused by photoirradiation, photoelectromotive force type photodiodes using a pn junction of a semiconductor, or the like.

The first light source 71 comprises a light emitting element 81 that emits the first light, and a lens 82 that shapes the first light emitted by the light emitting element 81 into parallel light or the like. The light emitting element 81 is, for example, a semiconductor element, such as a LED (light emitting diode) or an LD. The light emitting element 81 emits, for example, a light (hereinafter referred to as blue light) consisting of blue color component, and is the semiconductor element such as the light emitting diode (LED) or the LD comprising a light emitting spectrum including blue color component. In this way, the first light source 71 emits the blue light. The blue light is also referred to as a light showing blue.

The second light source 72 comprises a light emitting element 83 that emits the second light, and the lens 84 that shapes the second light emitted from the light emitting element 83 into parallel light or the like. The light emitting element 83 is, for example, the semiconductor element, such as the light emitting diode (LED) or the LD. The light emitting element 83 emits, for example, light (hereinafter referred to as violet light) consisting of a violet color component, and is the semiconductor element such as the light emitting diode (LED) or the LD comprising the light emitting spectrum including the violet color component. In this way, the second light source 72 emits the violet light.

The third light source 73 comprises a light emitting element 86 that emits the third light and a lens 87 that shapes the third light emitted from the light emitting element 86 into parallel light or the like.

The light emitting element 86 emits, for example, a light including two color components having different wavelengths as the third light. The light emitting element 86 has, for example, a light emitting element 86*a* that emits an excitation light and a fluorescent body 86*b* that emits the light including two color components having different wavelengths by an incidence of the excitation light emitted from the light emitting element 86*a*.

The third light source 73 is, for example, a light source that emits light (hereinafter referred to as green light) consisting of a green component including two color components having different wavelengths in which the first color component is green and the second color component is red. The green light is also referred to as light showing green.

For example, the excitation light emitted from the light emitting element 86a is the blue light having a peak at about 445 nm and the light emitted from the fluorescent body 86b is a broadband green light including the red component other than the green component. The light consisting of the red component is called red light and the red light is also referred to as a light showing red.

In addition, the light emitting element 86 may emit, for example, the green light including two color components in which the first color component having different wavelengths is green and the second color component is red. In this case, the light emitting element 86 is, for example, the semiconductor element such as the LED (light emitting diode) or the LD.

The above-described two color components having different wavelengths mean that the number of separable color components is two. Here, as above-described, the blue light is light having a wavelength of about 440 nm or more and less than about 490 nm. The green light is light having a wavelength of about 490 nm or more and less than about 600 nm. The red light is light having a wavelength of about 600 nm or more and less than about 680 nm. For example, light having a wavelength range of 490 nm to 700 nm includes the above-described green light and red light. For example, light having a wavelength range of 440 nm to 600 nm includes the above-described blue light and green light.

In two or more light sources having different dominant wavelengths, the different dominant wavelength means that peak wavelengths of the light emitted from each light sources are different from each other or in a case where there is no peak wavelength, central wavelengths are different from each other. The same range of the peak wavelength or the central wavelength is appropriately determined according to the specification or the like of the endoscope system 10.

The fourth light source 74 comprises a light emitting element 88 that emits the fourth light and a lens 89 that shapes the fourth light emitted from the light emitting element 88 into parallel light or the like. The light emitting element 88 emits, for example, a light with a specific wavelength (hereinafter referred to as a specific light) and is the semiconductor element such as the light emitting diode (LED) or the LD comprising the light emitting spectrum including the specific light.

It is preferable that the specific light is a narrow-band due to limited use. The narrow-band refers to a wavelength band which is narrow to an extent to be mostly regarded as a single wavelength in the endoscope system 10. For example, the narrow-band is a wavelength band with a width of several tens nm with respect to a center wavelength.

The fourth light source 74 can be used to obtain information that can be quantified and digitized from image information in addition to simple observation image regarding an object in the endoscope system 10.

In addition, the specific light having narrow-band is also used to acquire various observation images. For example, there are an observation image (hereinafter referred to as a specific depth emphasizing image) in which a tissue or a structure at a specific depth is selectively emphasized, and an observation image (hereinafter referred to as a deep blood vessel emphasizing image) in which thick blood vessels (hereinafter referred to as a deep blood vessel) in a particularly deep submucosal region is emphasized. In addition to this, there is a narrow-band observation image as the observation image. The narrow-band observation image is an observation image obtained by imaging the observation target using blue narrow-band light and green narrow-band light, and emphasizing a blood vessel or the like using the obtained captured image.

Figure 15:
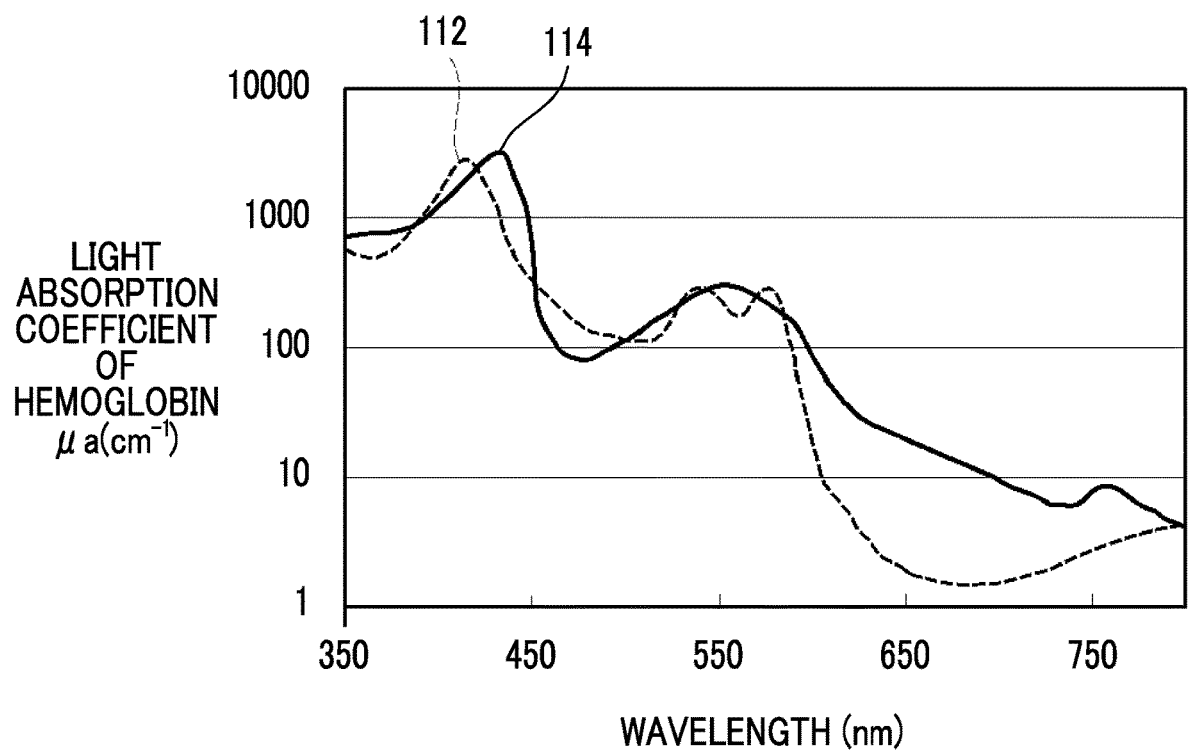
FIG. 15 is a graph illustrating light absorption coefficient of oxidized hemoglobin and reduced hemoglobin.

In addition, the narrow-band light is used for the measurement of oxygen saturation. The narrow-band light is light having a wavelength in which the difference between a light absorption coefficient of oxidized hemoglobin and a light absorption coefficient of reduced hemoglobin is large, at the central wavelength. As shown in FIG. 15 to be described, for example, the difference between the light absorption coefficient of oxidized hemoglobin and the light absorption coefficient of reduced hemoglobin becomes larger at a wavelength of about 470 nm. The narrow-band light with a center wavelength of about 470 nm can be used for measuring oxygen saturation.

In the normal observation mode, the light source control unit 22 turns on the first light source 71 and the third light source 73, and does not turn on the second light source 72 and the fourth light source 74. Meanwhile, in the blood vessel emphasis observation mode, the light source control unit 22 turns on all the first light source 71, the second light source 72, and the third light source 73.

In a case where the third light source 73 emits the green light in which the first color component is green and the second color component is red and the first light source 71 emits the blue light, in the normal observation mode, light including the green light and the red light emitted by the third light source 73 and the blue light emitted by the first light source 71 are multiplexed to generate broadband white light. Meanwhile, in the blood vessel emphasis observation mode, mixed light in which violet light having a high absorbance for hemoglobin in blood is mixed with the white light is generated. In addition, in the blood vessel emphasis observation mode, the light source control unit 22 lowers the ratio of the quantity of the blue light such that the violet light becomes more dominant than the blue light.

The fourth light source 74 may irradiate a light of color component having a different wavelength from above-described the first light source 71, the second light source 72, and the third light source 73. The combination of the light emitted from above-described the first light source 71, the second light source 72, the third light source 73, and the fourth light source 74 is not particularly limited to that described above.

In addition, above-described the first light source 71, the second light source 72, the third light source 73, and the fourth light source 74 are not limited to the above-described configuration. The semiconductor light source and the fluorescent body that emits the light of another color as excitation light which is the light emitted from the semiconductor light source, and the like may be used in combination. A lamp light source such as a xenon lamp may also be used. Additionally, the light source may have a configuration in which the semiconductor light source, the semiconductor light source and the fluorescent body, the lamp light source, and an optical filter for adjusting the wavelength band or the spectral spectrum are combined. For example, the light source may have a configuration in which a white LED and an optical filter are combined.

Figure 6:
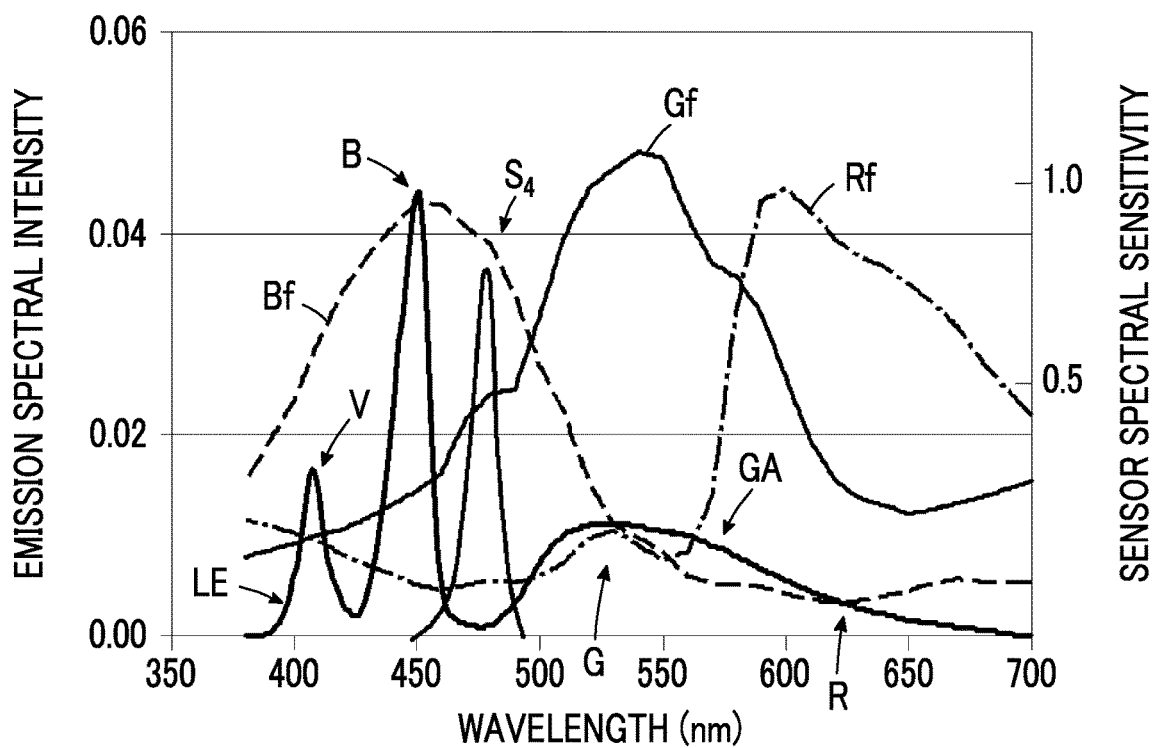
FIG. 6 is a graph illustrating an example of a light emitting spectrum of the light source unit and spectral sensitivity of the image sensor in the endoscope system of the embodiment of the invention.

In the light source device 14 having the above-described configuration, the light emitted from the light source unit 20 of the light source device 14, that is, the illumination light Ls (refer to FIG. 5), which passes through the light guide 41 of the endoscope 12 and is emitted from the distal end part 12d of the endoscope, has, for example, a light emitting spectrum LE illustrated in FIG. 6.

Here, FIG. 6 is a graph illustrating an example of the light emitting spectrum of the light source unit and the spectral sensitivity of the image sensor in the endoscope system of the embodiment of the invention.

In addition, in the light emitting spectrum LE illustrated in FIG. 6, a symbol V indicates the violet light, a symbol B indicates the blue light, a symbol G indicates the green light, and a symbol R indicates the red light. A symbol GA indicates a color including green light and red light. A symbol $S_4$ indicates the light of a wavelength of about 470 nm emitted from the fourth light source. Additionally, in the light emitting spectrum LE illustrated in FIG. 6, a solid line indicates that the light quantity is relatively low, and a dashed line indicates that the light quantity is relatively high.

The light emitting spectrum LE illustrated in FIG. 6, has a peak wavelength near the wavelength of 400 nm and a peak wavelength near the wavelength of 450 nm. The peak wavelength near the wavelength of 400 nm is based on the violet light emitted from the second light source 72, and the peak wavelength near the wavelength of 450 nm is based on the blue light emitted from the first light source 71.

Light having a wavelength of 470 nm to 700 nm is based on the green light emitted from the third light source 73, and includes green and red as color components.

The light emitting spectrum LE illustrated in FIG. 6 represents substantially white light. In the endoscope system 10, the observation object is imaged using the image sensor 48 having spectral sensitivity characteristics illustrated in FIG. 6 by the reflected light Lr of the illumination light Ls having the light emitting spectrum LE including the blue light, the green light, and the red light. A symbol Bf illustrated in FIG. 6 indicates the spectral sensitivity for the light showing blue color. A symbol Gf represents the spectral sensitivity for the light showing green color. A symbol Rf represents the spectral sensitivity for the light showing red color. The spectral sensitivity Bf and the spectral sensitivity Gf have an overlapping wavelength range, and the spectral sensitivity Gf and the spectral sensitivity Rf have an overlapping wavelength range. The spectral sensitivity is not limited thereto.

The image sensor 48 has the first element part 48a, the second element part 48b, and the third element part 48c as described above. For example, the first element part 48a has the spectral sensitivity Gf for the light showing green color. The second element part 48b has the spectral sensitivity Rf for the light showing red color. The third element part 48c has the spectral sensitivity Bf for the light showing blue color.

Additionally, the first light source 71 may be configured to have the light emitting diode having a light emitting peak between the peak wavelength of the spectral sensitivity of the first element part 48a and the peak wavelength of the spectral sensitivity of the second element part 48b. In this case, in a case where the first element part 48a is the spectral sensitivity Gf and the second element part 48b is the spectral sensitivity Rf, a light emitting diode having a light emitting peak in a wavelength of 550 to 600 nm is used. In a case where the first element part 48a has the spectral sensitivity Bf and the second element part 48b has the spectral sensitivity Gf, a light emitting diode having a light emitting peak in a wavelength of 450 to 550 nm is used.

In addition to the above configuration, as the light source, the first light source 71 may be a light source that emits red light, the second light source 72 may be a light source that emits green light, and the third light source 73 may be a light source that emits blue light.

The observation object is imaged using the light emitted from at least first light source 71 of the light source unit 20, and the first signal value of the first color component obtained from the first element part 48a of the image sensor 48 and the second signal value of the second color component obtained from the second element part 48b are obtained in the processor device 16. The processor device 16 obtains a signal ratio between the first signal value and the second signal value, and sets the signal ratio to predetermined set value by changing at least one of the first signal value or the second signal value.

In the image sensor 48, the first signal value of the first color component is obtained in the first element part 48a, the second signal value of the second color component is obtained in the second element part 48b, and the third signal value of a color component other than the two color components is obtained in the third element part 48c.

Then, the first signal value and the second signal value are output from the DSP 56 to the correction quantity calculation unit 60. The signal ratio between the first signal value and the second signal value is obtained in the correction quantity calculation unit 60, and the signal ratio is set to a predetermined set value by changing at least one of the first signal value or the second signal value.

Additionally, the signal ratio may be set to the predetermined set value by changing at least one of the first signal value, the second signal value, or the third signal value according to the light quantity. In this case, it is determined to change which signal value among the first signal value, the second signal value, and the third signal value depending on the light quantity, a changing value is obtained as a correction coefficient, and the correction coefficient is stored in the correction quantity calculation unit 60.

For example, the brightness value is calculated using at least one of the first signal value, the second signal value, or the third signal value, and the light quantity of the first light source 71 is specified on the basis of the brightness value. Also, any one signal value of the first signal value, the second signal value, or the third signal value is set as a reference value, and then the signal ratio may be set to the predetermined set value by changing at least one of the first signal value, the second signal value, or the third signal value according to the light quantity. As described, setting a signal value to a set value is referred to as a white balance processing. The tone of the endoscopic image can be kept constant regardless of the light quantity by the white balance processing.

In this case, in the correction quantity calculation unit 60, the first signal value, the second signal value, or the third signal value to be used as the reference value is determined, the first signal value, the second signal value, or the third signal value to be changed according to the light quantity are determined, a changing value is obtained as a correction coefficient, and the correction coefficient is stored in the correction quantity calculation unit 60.

One signal value is used as the reference value in the above description, but the invention is not limited thereto. The signal ratio may be set to the predetermined set value by changing at least one of the first signal value, the second signal value, or the third signal value according to the light quantity without setting the reference value.

Figure 7:
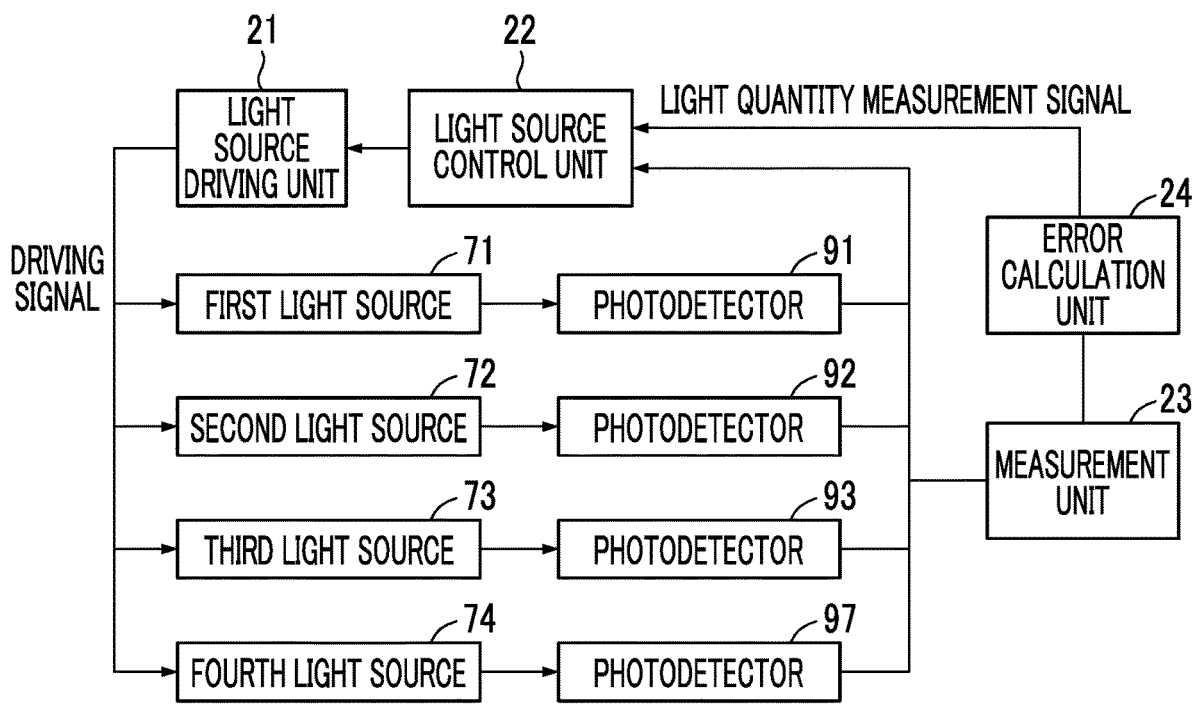
FIG. 7 is a schematic view illustrating an example of a configuration for performing light quantity control.

FIG. 7 is a schematic view illustrating an example of a configuration for performing light quantity control.

Each of the photodetectors 91, 92, 93, and 97 receives light reflected by the beam splitters 94, 95, 96, and 98, outputs a light quantity measurement signal according to each light quantity of received light as illustrated in FIG. 7 and outputs the light quantity measurement signal to the light source control unit 22.

The light source control unit 22 compares the light quantity measurement signal and a light quantity to be a target (hereinafter simply referred to as the target light quantity), and performs a feedback control adjusting the driving signal which is supplied to the first light source 71, the second light source 72, the third light source 73, and the fourth light source 74 in the light source driving unit 21 such that the light quantity meets the target light quantity value based on the comparison result. The feedback control illustrated in FIG. 7 is called Auto Power Control (APC). In the light source control unit 22, the target light quantity is stored or the target light quantity value is input from the control unit 69.

As described above, the individual light quantities of the first light source 71, the second light source 72, the third light source 73, and the fourth light source 74 are constantly monitored by the photodetectors 91, 92, 93, and 97, and by adjusting the drive signal to be applied based on the measurement result of the light quantity, the light quantity can be controlled so as to be kept at the target quantity value. The measurement accuracy of the light quantity is high because the return light is suppressed. Therefore, it is possible to stably obtain illumination light of a target light emitting spectrum with higher accuracy. In addition, the configuration of the light source unit 20 is not limited to the configuration illustrated in the above-described FIG. 5.

Also, a measurement unit 23 connected to each of the photodetectors 91, 92, 93, and 97 and an error calculation unit 24 connected to the measurement unit 23 are provided. The measurement unit 23 and the error calculation unit 24 are used in the control method of the embodiment of the present invention. The control using the above-described APC and the measurement unit 23 and the error calculation unit 24 can be appropriately switched according to the control method. In addition, the control using the above-described APC and the measurement unit 23 and the error calculation unit 24 may be combined.

The measurement unit 23 obtains an integrated light quantity obtained by the photodetector in the predetermined error calculation period after turning on the light source. The error calculation period is set, for example, with respect to an exposure period indicating the total time during which the light source emits light. The error calculation period is, for example, half of the exposure period, and the time is counted after turning on the light source.

The error calculation unit 24 obtains a difference between the integrated light quantity obtained by the measurement unit and the target light quantity.

Therefore, in the error calculation unit 24, the target light quantity is stored in advance or the target light quantity value stored in the light source control unit 22 is input.

One measurement unit 23 and one error calculation unit 24 are provided, but the measurement unit 23 and the error calculation unit 24 may be provided in each of the photodetectors 91, 92, 93, and 97. In this case, the measurement unit and the error calculation unit are provided according to the number of the photodetectors.

Control Method of Endoscope System

Next, a control method of the endoscope system 10 will be described.

In the endoscope system 10, for example, in a case where the fourth light source 74 emits the green light in which the first color component is green and the second color component is red and the first light source 71 emits the blue light, the light including the green light and the red light emitted by the fourth light source 74 and the blue light emitted by the first light source 71 are multiplexed in normal-observation mode to generate broadband white light. The white light is incident on the light guide 41 and is emitted from the light guide 41 as illumination light Ls (see FIG. 5) to the object Ob.

Additionally, in the multi-frame observation mode, the light source control unit 22 changes the wavelength range or the spectral spectrum of the illumination light for each imaging frame for obtaining the plurality of captured images to be used to generate the observation image as a result of the control of the above-described each light source. Also, the term "turning on the light" means that light is turned on to such an extent that the image sensor 48 can image the observation object, that is the image to be observed can be recognized in the observation image. "Turning off the light" is also referred to as "on".

"Turning on the light" means not only completely blocking the light emitting, but also reducing the light quantity to such an extent that the image sensor 48 can image the observation object.

"Turning off the light" is also referred to as "off".

As described above, the multi-frame observation mode is to generate one observation image using the plurality of captured images. In this case, to obtain the plurality of captured images, for example, the first illumination light and the second illumination light are emitted from different light sources. Turning on the light source in the light source unit 20 in the multi-frame observation mode is also referred to as a multi-frame lighting.

In the case of the multi-frame lighting control, is necessary that illumination light Ls is completely turned on and off. Therefore, a turned off state of the illumination light Ls inevitably occurs. When the illumination light Ls is converted from turned on to turned off, overshoot or delay can easily occur.

In addition, the light source unit 20 needs to control light quantity in a wide dynamic range depending on the subject distance, and the overshoot condition differs depending on a light region. Therefore, it is difficult to optimize a control condition or the driving circuit characteristics constituting the light source driving unit 21.

In the endoscope system 10, the image to be observed is acquired for each illumination light using the control method to be described below.

As described above, the light source unit 20 of the endoscope system 10 provides a feedback control function called APC as illustrated in FIG. 7 with respect to each light source as described above. However, APC cannot cope with the overshoot and light emitting delay that occur in a short period such as one frame for obtaining one image, for example. According to the present invention, even if the image to be observed for each illumination light is acquired by completely turning off and turning on the illumination light by the light source, it is possible to make the mutual image signal ratio constant in the plurality of images by performing a following control.

In the control method, the photodetector for monitoring the light quantity of each light source is composed of, for example, a photodiode (PD). An electric current corresponding to the light quantity generated by the photodiode is voltage-converted, and further converted into a 16-bit digital value by an Analog-to-Digital Converter (ADC), for example.

The target quantity light is also input as the 16-bit digital value. After comparing the target light quantity and a PD light reception value among the 16 bits, the feedback control is performed so as to eliminate the error. For example, the exposure period is 10 ms, and the light quantity monitor and the APC are continuously performed with a sampling period of 100 μs.

Figure 8:
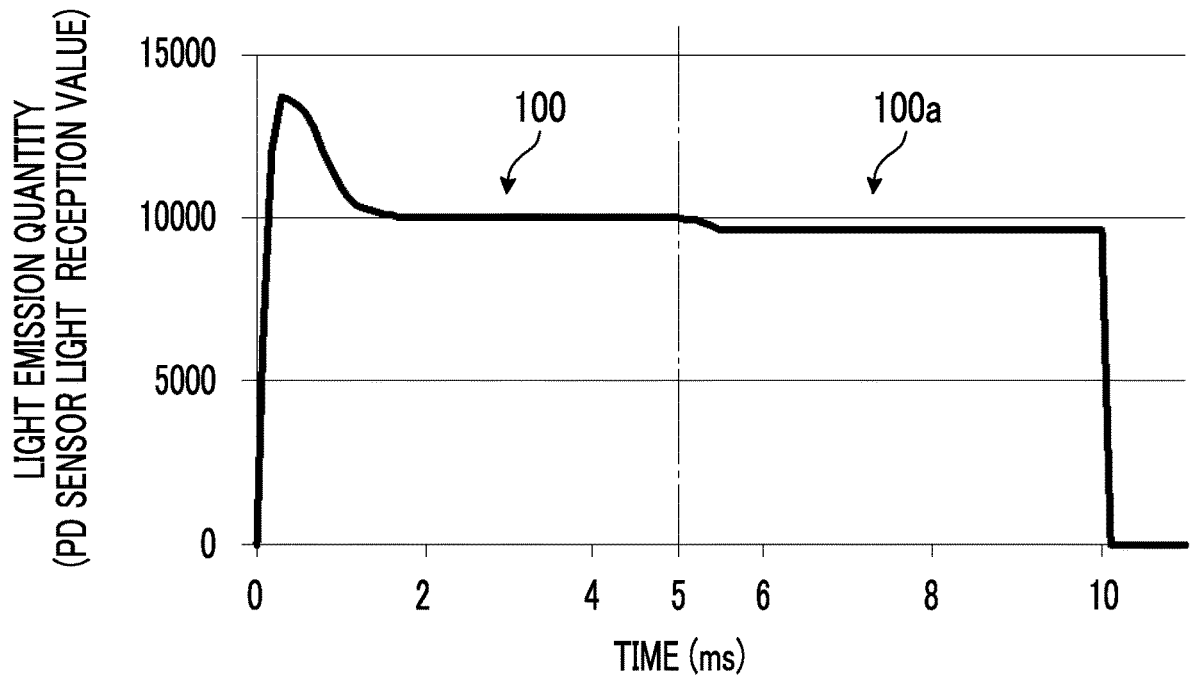
FIG. 8 is a graph illustrating a first example of a control method of the endoscope system of the embodiment of the invention.
Figure 13:
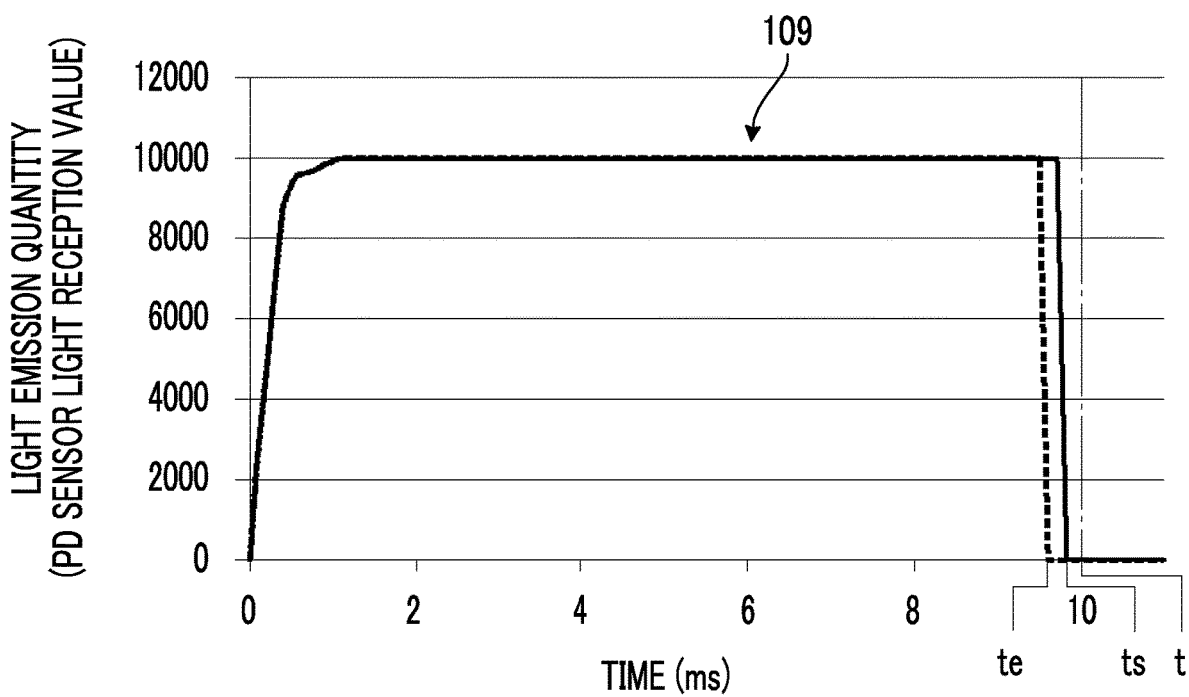
FIG. 13 is a graph illustrating a sixth example of the control method of the endoscope system of the embodiment of the invention.

FIG. 8 and FIG. 13 are graphs for explaining the control method of the endoscope system of the embodiment of the invention.

Adjustment of Target Light Quantity

The light source control unit 22 changes a target light quantity after an error calculation period according to a difference obtained by an error calculation unit 24 and thus, makes an integral light quantity in a predetermined exposure period constant. In this case, the target light quantity is calculated by the light source control unit 22 based on the difference obtained by the error calculation unit 24. In a case where the predetermined error calculation period is, for example, half of the exposure period after turning on the above-described light sources, the target light quantity is adjusted using an integrated light quantity in a photodetector in half of the exposure period. Adjustment of the target light quantity includes both of increasing the target light quantity and reducing the target light quantity.

Specifically, for example, in a case where the light emitting is started at target light quantity of 10000, light emitting characteristics of the light source cannot be handled by the APC right after the light is turned on. Therefore, excessive light emitting which means that the light quantity becomes bigger than the target light quantity such as a light quantity waveform 100 as shown in FIG. 8, so-called overshoot, occurs. After that, light converges to the target light quantity by APC.

Here, the error calculation period is set until 5.0 ms from when the light is turned on and the light quantity integrated value is calculated for each of sampling cycle 100 μs. The light quantity integrated value is, for example, 520300 in the error calculation period. Here, in a case where the target light quantity integrated value in the error calculation period is 500000, the difference of 4.1% occurs between the actually emitted light quantity integrated value and the target light quantity integrated value.

Therefore, after the error calculation period has passed, the integral light quantity in the exposure period can be adjusted to the target value by changing the target light quantity in the region 100a from 10000 to for example, 9594.

Figure 9:
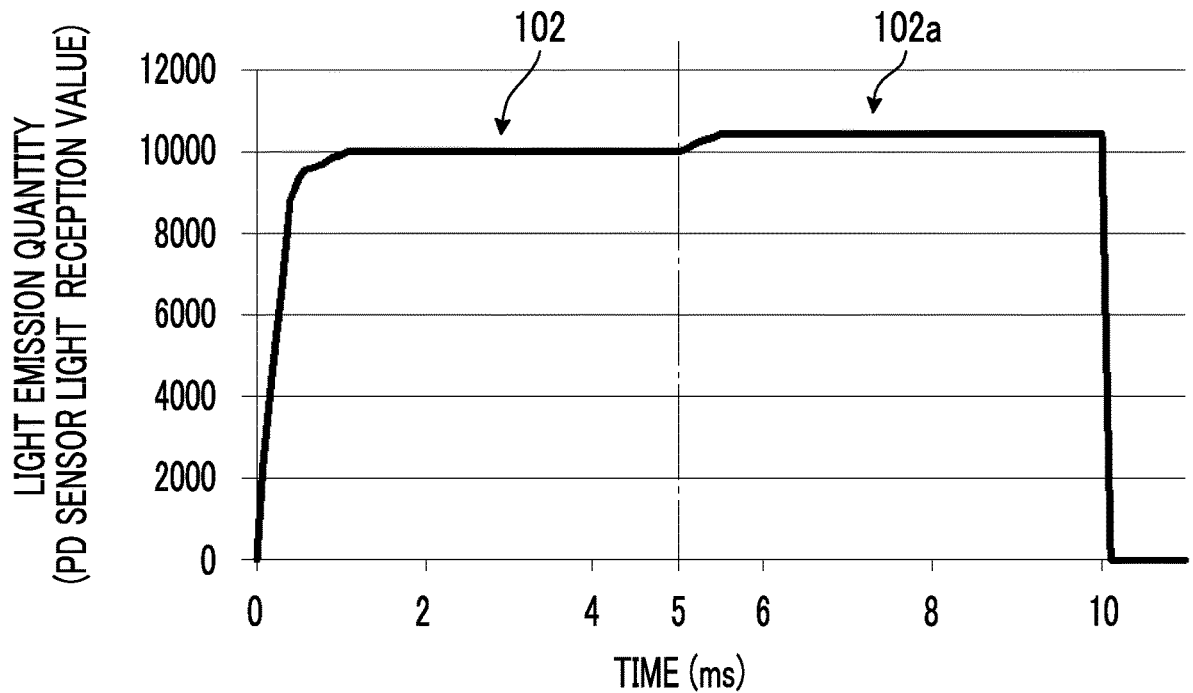
FIG. 9 is a graph illustrating a second example of the control method of the endoscope system of the embodiment of the invention.

In addition, for example, in a case where the light emitting is started at the target light quantity 10000, the light emitting characteristics of the light source cannot be handled by the APC right after the light is turned on, and the light emitting delay occurs such as a light quantity waveform 102 as shown in FIG. 9. After that, the light converges to the target light quantity by the APC.

Here, the error calculation period is set until 5.0 ms from when the light is turned on and the light quantity integrated value is calculated for each of sampling cycle 100 μs. The light quantity integrated value is, for example, 479800 in the error calculation period. Here, in a case where the target light quantity integrated value in the error calculation period is 500000, the difference of −4.1% occurs between the actually emitted light quantity integrated value and the target light quantity integrated value.

Therefore, after the error calculation period has passed, the integral light quantity in the exposure period can be adjusted to the target value by changing the target light quantity in the region 102a from 10000 to for example, 10404.

Further, in the present invention, it is not limited that the control is performed for each photoirradiation of the light source, and the control may be performed for a plurality of photoirradiation of the light source. In this case, the light source control unit 22, for example, changes the target light quantity of the second illumination light according to the difference acquired by the error calculation unit in the first illumination light to make the ratio of the integral light quantity in the predetermined exposure period constant in the plurality of images. Also, the change of the target light quantity is performed by not only on two of the first illumination light and the second illumination light, but also on a third illumination light and subsequent illumination light according to the difference obtained by the error calculation unit in the first illumination light. The change of the target light quantity of the second illumination light by the first illumination light may be repeatedly controlled as one repeating unit.

Adjustment of Timing of Turning Off Light

Further, the light source control unit 22 changes timing of the turning off the light source after an error calculation period according to a difference obtained by the error calculation unit 24 to make an integral light quantity in the predetermined exposure period constant. In this case, the timing for turning off the light is calculated from the light source control unit 22 based on the difference obtained by the error calculation unit 24. In a case where the predetermined error calculation period is, for example, half of the exposure period after turning on the above-described light sources, the timing of turning off the light is changed using the integrated light quantity in the photodetector in half of the exposure period. That is, the timing of turning off the light is determined. A change of the timing of turning off the light includes both to turn off the light early and to turn off the light late.

Figure 10:
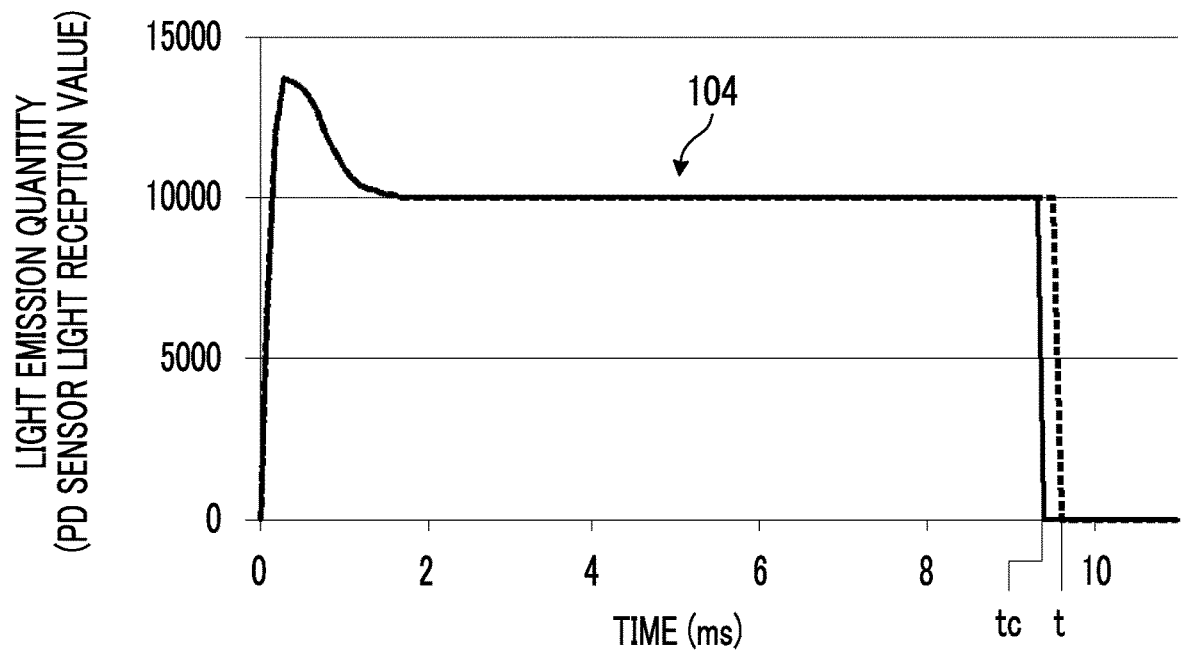
FIG. 10 is a graph illustrating a third example of the control method of the endoscope system of the embodiment of the invention.

Specifically, for example, in a case where the light emitting is started at the target light quantity 10000 and the overshoot occurs such as a light quantity waveform 104 as shown in FIG. 10, the error calculation period is set until 5.0 ms from when the light is turned on and the light quantity integrated value is calculated for each of sampling cycle 100 μs. The light quantity integrated value is, for example, 520300 in the error calculation period. As described above, in a case where the target light quantity integrated value in the error calculation period is 500000, the difference of 4.1% occurs between the actually emitted light quantity integrated value and the target light quantity integrated value. In order to compensate for the difference, for example, the integral light quantity in the exposure period can be adjusted to the target value by advancing timing for turning off the light by 0.2 ms. In FIG. 10, time t indicates set exposure time, and time tc indicates corrected exposure time. In this case, the exposure time is shortened by 0.2 ms.

Figure 11:
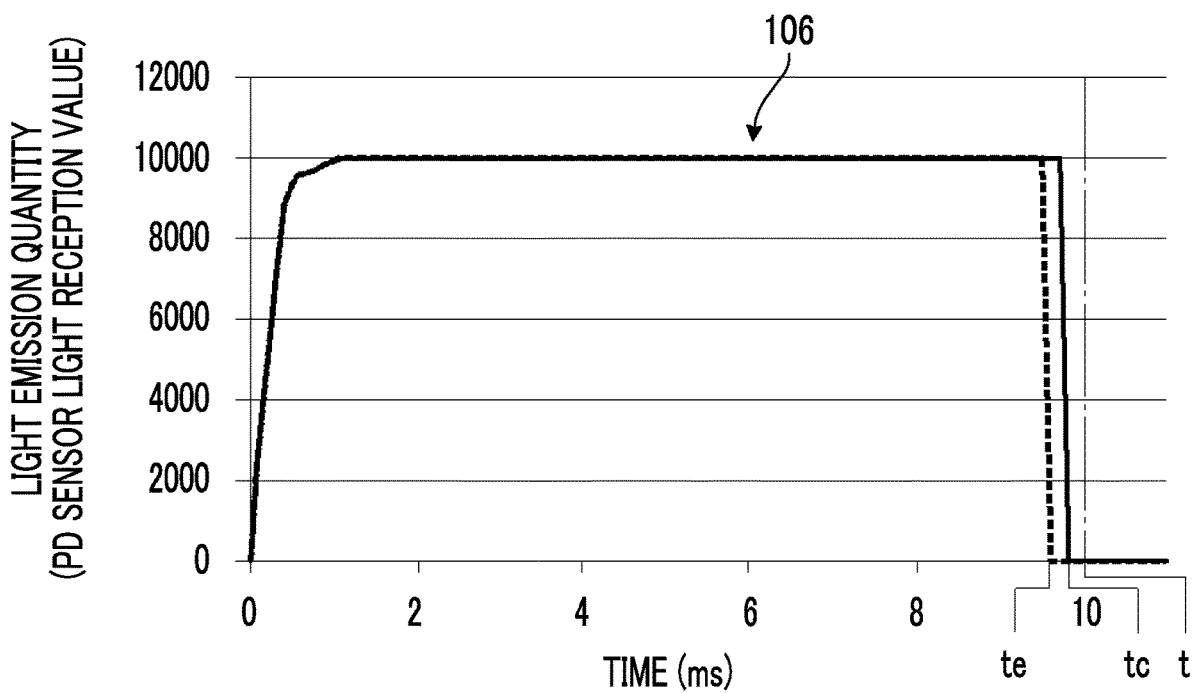
FIG. 11 is a graph illustrating a fourth example of the control method of the endoscope system of the embodiment of the invention.

Further, for example, in a case where the light emitting is started at the target light quantity 10000, and the light emitting delay occurs such as a light quantity waveform 106 as shown in FIG. 11, the error calculation period is set until 5.0 ms from when the light is turned on and the light quantity integrated value is calculated for each of sampling cycle 100 μs. The light quantity integrated value is, for example, 479600 in the error calculation period. As described above, in a case where the target light quantity integrated value in the error calculation period is 500000, the difference of −4.0% occurs between the actually emitted light quantity integrated value and the target light quantity integrated value. In order to compensate for the difference, for example, the integral light quantity in the exposure period can be adjusted to the target value by delaying timing for turning off the light by 0.2 ms. In addition, in FIG. 11, the time t indicates the set exposure time, and time to indicates light emitting time in a standard state which is not corrected. The exposure time is set longer than the light emitting time and thus, a correction period is set. The time tc indicates the corrected exposure time. In this case, the corrected exposure time is 0.2 ms longer than the light emitting time.

Additionally, in a case where the exposure time is used, it is not necessary to change the target light quantity during the light emitting, and feedback control of the target light quantity is unnecessary.

Further, in the present invention, it is not limited that the control is performed for each photoirradiation of the light source, and the control may be performed for a plurality of photoirradiation of the light source. In this case, the light source control unit 22, for example, changes the timing of turning off the second illumination light according to the difference obtained by the error calculation unit in the first illumination light to make the ratio of integral light quantity in the predetermined exposure period constant in the plurality of images. Also, the change of the timing of turning off is performed by not only on two of the first illumination light and the second illumination light, but also on a third illumination light and subsequent illumination light according to the difference obtained by the error calculation unit in the first illumination light. The change of the timing of turning off the second illumination light by the first illumination light may be repeatedly controlled as one repeating unit.

Adjustment of Exposure Period

Further, a light source control unit 22 changes the predetermined exposure period according to a difference obtained by an error calculation unit 24 to make the integral light quantity in the exposure period constant. In this case, a change of the exposure period is calculated from the light source control unit 22 based on the difference obtained by the error calculation unit 24.

In a case where the predetermined error calculation period is, for example, half of the exposure period after turning on the above-described light sources, the exposure period is changed using the integrated light quantity in the photodetector in half of the exposure period. The exposure period is adjusted, for example, by the shutter speed of the electronic shutter. Therefore, a signal for setting the shutter speed of the electronic shutter is output from the light source control unit 22 to an imaging control unit 70, and the shutter speed of the electronic shutter is adjusted by the imaging control unit 70.

Figure 12:
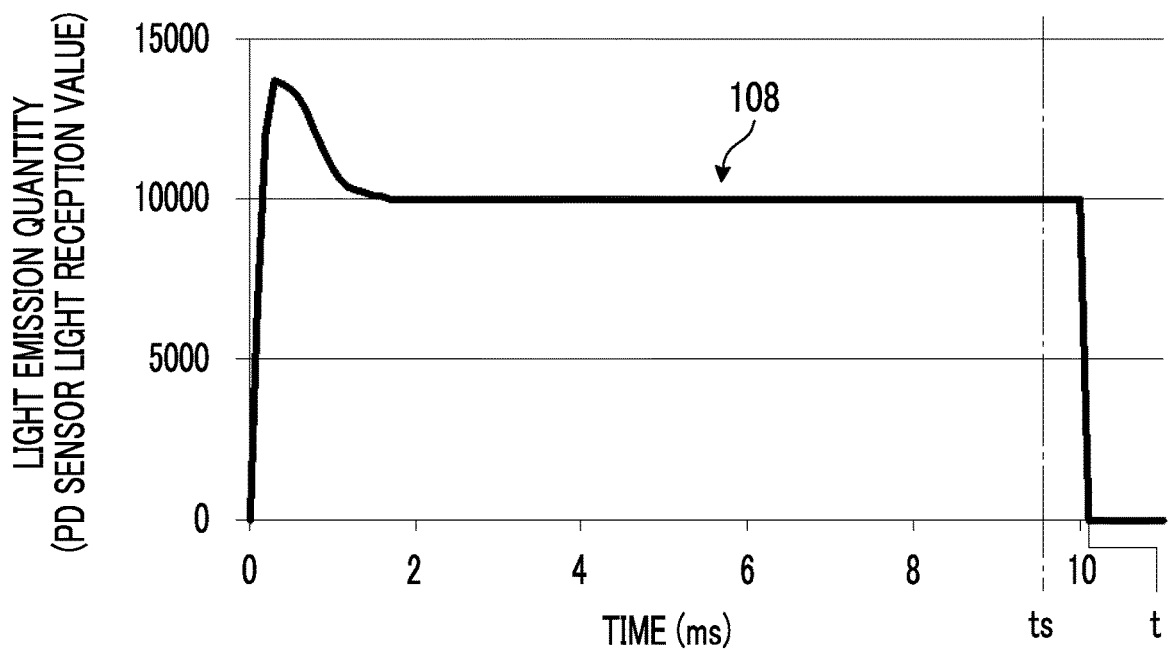
FIG. 12 is a graph illustrating a fifth example of the control method of the endoscope system of the embodiment of the invention.

Specifically, with respect to a light quantity waveform 108 in which overshoot occurs as shown in FIG. 12, for example, the error calculation period is set until 5.0 ms from when the light is turned on and the light quantity integrated value is calculated for each of sampling cycle 100 μs. The difference between the actually emitted light quantity integrated value in the error calculation period and the target light quantity integrated value is obtained. The electronic shutter time is adjusted to compensate for the difference. In this case, in a case where the difference is 4.1%, for example, the electronic shutter is closed 0.2 ms earlier to compensate for the difference. That is, the shutter speed of the electronic shutter is increased. Thus, the integral light quantity in the exposure period can be adjusted to the target value. Additionally, the time t indicates a set exposure time, and time is indicates the time to close a corrected electronic shutter in FIG. 12. In this case, the time to close the corrected electronic shutter is advanced by 0.2 ms.

Further, with respect to a light quantity waveform 109 in which the light emitting delay occurs as shown in FIG. 13, for example, the error calculation period is set until 5.0 ms from the start of turning on the light and the light quantity integrated value is calculated for each of sampling cycle 100 μs. The difference between the actually emitted light quantity integrated value in the error calculation period and the target light quantity integrated value is obtained. The electronic shutter time is adjusted to compensate for the difference. In this case, in a case where the difference is −4.0%, for example, the electronic shutter is closed 0.2 ms later and closed to compensate for the difference. That is, the shutter speed of the electronic shutter is reduced. Thus, the integral light quantity in the exposure period can be adjusted to the target value. Furthermore, in FIG. 13, the time t indicates the set exposure time, and the time to indicates a light emitting time in the standard state which is not corrected. The exposure time is set longer than the light emitting time and thus, the correction period is set. Time is indicates the time to close the corrected electronic shutter. In this case, the time to close the corrected electronic shutter is deferred by 0.2 ms.

In a case where the electronic shutter is used, it is not necessary to change the target light quantity during the light emitting, and feedback control of the target light quantity is unnecessary.

Further, in the present invention, it is not limited that the control is performed for each photoirradiation of the light source, and the control may be performed for a plurality of photoirradiation of the light source. In this case, the light source control unit 22, for example, changes the exposure period of second illumination light according to the difference acquired by the error calculation unit in first illumination light to make the ratio of the integral light quantity in the predetermined exposure period constant in the plurality of images. Also, the change of the exposure period is performed by not only on two of the first illumination light and the second illumination light, but also on a third illumination light and subsequent illumination light according to the difference obtained by the error calculation unit in the first illumination light. The change of the exposure period of the second illumination light by the first illumination light may be repeatedly controlled as one repeating unit.

In any control method illustrated in above-described FIGS. 8 to 13 is not limited that each image is controlled as described above, and the plurality of images can be controlled. This makes it possible to make the ratio of the integral light quantity constant in the plurality of images over the plurality of images.

Figure 14:
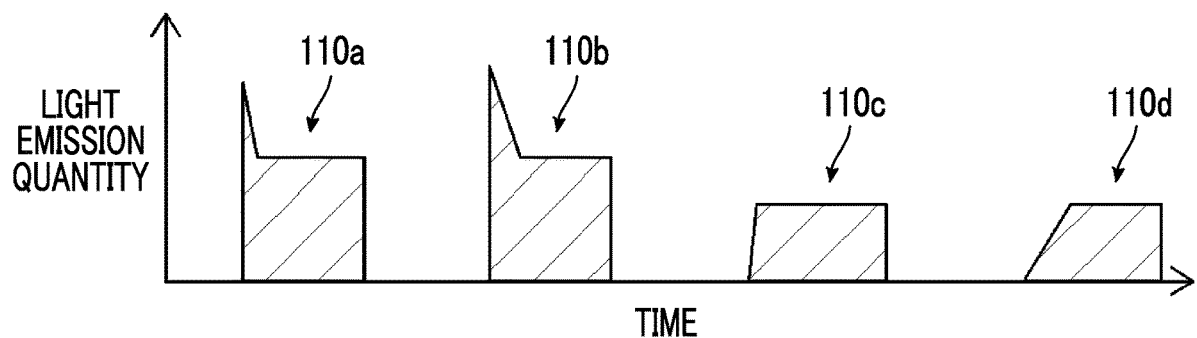
FIG. 14 is a graph illustrating an example of a light emitting state of illumination light using the light source unit of the endoscope system of the embodiment of the invention.

For example, as shown in FIG. 14, an image signal ratio of a first image obtained from first illumination light of the overshoot first light quantity waveform 110a and an image signal ratio of a second image obtained from second illumination light of a second light quantity waveform 110b can be kept constant.

Further, as illustrated in FIG. 14, an image signal ratio of a first image obtained from first illumination light of a first light quantity waveform 110c in which a light emitting delay occurred and the image signal ratio of a second image obtained from second illumination light of a second light quantity waveform 110d can be kept constant. In this way, it is possible to enhance the accuracy of quantification and digitization such as oxygen saturation calculation.

FIG. 14 is a graph illustrating an example of the light emitting state of the illumination light by the light source unit of the endoscope system of the embodiment of the present invention.

In addition, since the illumination light is completely turned on and off, unnecessary light is not present at the time of image acquisition. Even if a complementary metal oxide semiconductor (CMOS) sensor is used for the image sensor 48, the occurrence of color mixture is suppressed and decline of measurement accuracy such as oxygen saturation is also suppressed.

In addition, in a case where a high output light source is adopted in the above-described light source, high output of the driving circuit and high speed response are generally difficult to be compatible, which may cause response delay of the light source.

However, according to the control method of the present invention, even though the response delay of the light source occurs, the mutual image signal ratio in the plurality of images can be kept constant.

As shown in FIG. 15, for example, at a wavelength of about 470 nm, the difference between light absorption coefficient 112 of oxidized hemoglobin and light absorption coefficient 114 of reduced hemoglobin becomes large. Thus, the narrow-band light source is the narrow-band light with a center wavelength of about 470 nm in the embodiment of the invention. As shown in FIG. 15, there is a wavelength in which the difference between the light absorption coefficient 112 of oxidized hemoglobin and the light absorption coefficient 114 of reduced hemoglobin is large in the violet, blue, or green wavelength band other than about 470 nm.

Therefore, a light source that emits narrow-band light centered on any one of these wavelengths is used.

An oxygen saturation image is provided by multi-frame observation mode. Hereinafter, the oxygen saturation image will be described.

The oxygen saturation image is created by an image processing unit 61 using two images of the first image and the second image. The first image is composed of a B1 image. The first image is an image obtained by a light having a center wavelength of about 470 nm emitted from a fourth light source 74 as the first illumination light.

The second image is composed of an R2 image, a G2 image, and a B2 image. The second image is an image obtained by the green light including the green and red color components emitted from a third light source 73 and a blue light emitted from a first light source 71 as the second illumination light.

The oxygen saturation image is created by the image processing unit 61 using the B1 image, the B2 image, the G2 image, and the R2 image.

For example, the ratio of B1 image with respect to G2 image (hereinafter referred to as signal ratio B1/G2) and the ratio of G2 image with respect to R2 image (hereinafter referred to as signal ratio R2/G2) are calculated for each pixel.

The signal ratio B1/G2 changes mainly depending on the value of the oxygen saturation and the blood volume of the observation object, and the signal ratio R2/G2 changes mainly depending on the blood volume of the observation object.

Using a correlation of the signal ratio B1/G2 and the signal ratio R2/G2, the oxygen saturation of the observation object for every pixel is calculated in accordance with the correlation of the signal ratio B1/G2 and the signal ratio R2/G2. Furthermore, the correlation of the signal ratio B1/G2 and the signal ratio R2/G2, and the oxygen saturation can be predetermined by simulation or the like.

Next, for example, the oxygen saturation image representing the oxygen saturation of the observation object by color is generated.

Specifically, a color observation image is generated using the B2 image, the G2 image, and the R2 image. After that, the oxygen saturation image is generated by coloring each pixel of the generated observation image according to the value of the oxygen saturation. The generated oxygen saturation image is displayed on a monitor 18 by being input to a display control unit 66.

Here, the configuration of a light source unit 20 is not limited to have the four light sources as illustrated in FIG. 5.

Figure 16:
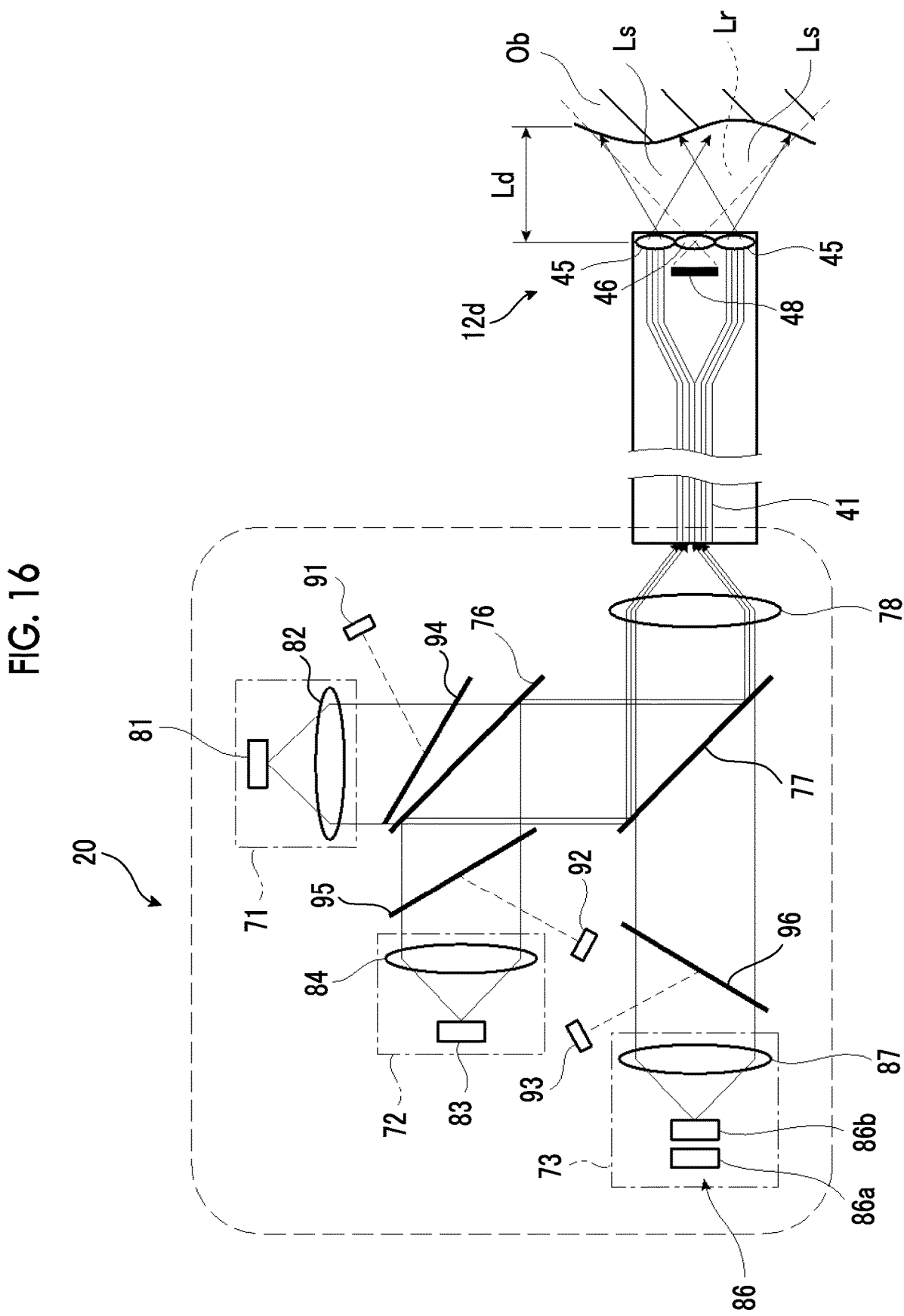
FIG. 16 is a schematic view illustrating a second example of the light source unit of the endoscope system of the embodiment of the invention.
Figure 17:
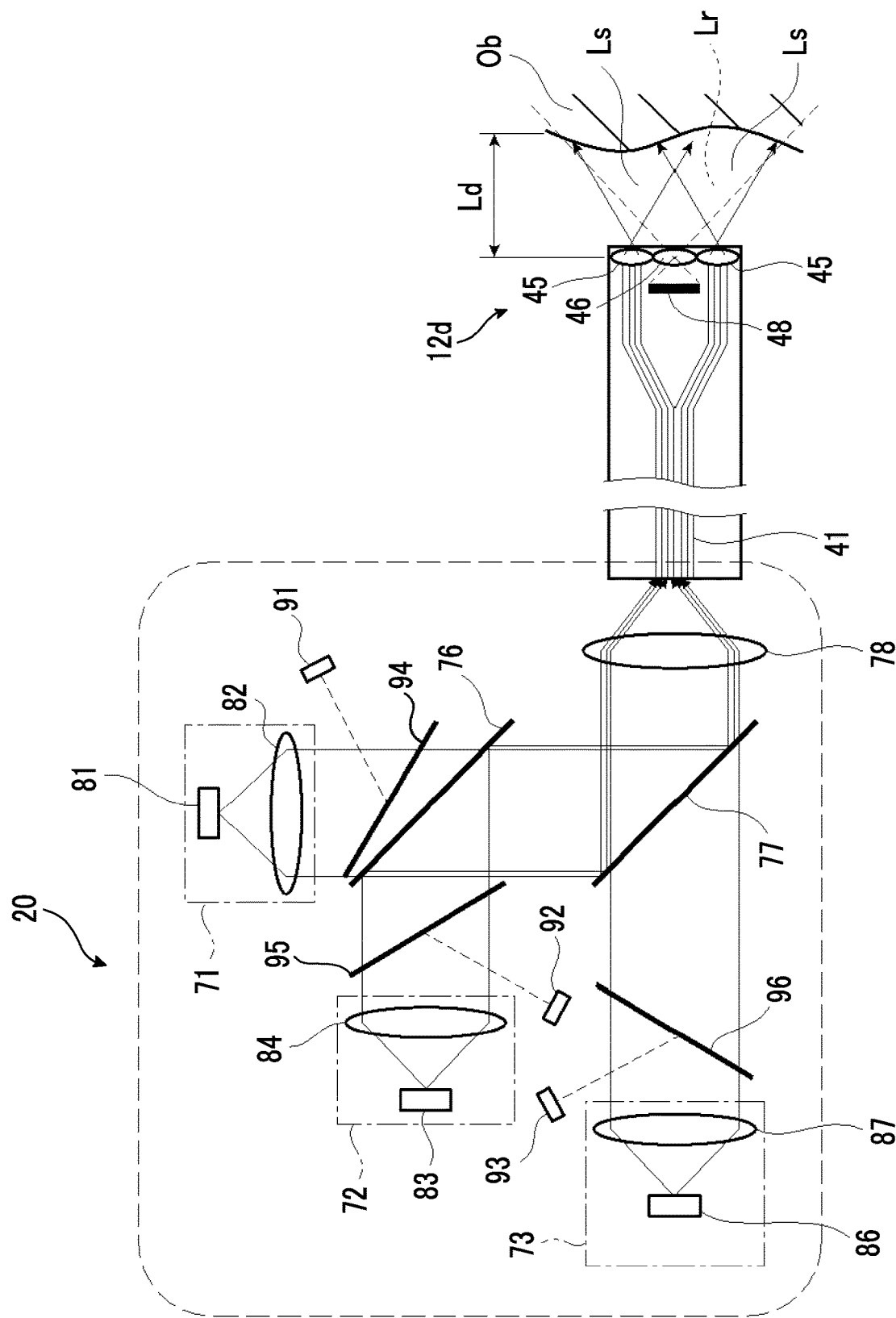
FIG. 17 is a schematic view illustrating a third example of the light source unit of the endoscope system of the embodiment of the invention.

FIG. 16 is a schematic view illustrating a second example of the light source unit of the endoscope system of the embodiment of the present invention, and FIG. 17 is a schematic view showing a third example of the light source unit of the endoscope system of the embodiment of the present invention.

In the light source unit 20 illustrated in FIGS. 16 and 17, the same components as the light source unit 20 shown in FIG. 5 will be designated by the same reference signs, and the detailed description will be omitted.

Any of light source unit 20 illustrated in FIGS. 16 and 17 has three light sources.

The light source illustrated in FIG. 16 is different from the light source unit 20 shown in FIG. 5 in that the fourth light source 74 is not provided, and the other configuration is the same as the light source unit 20 shown in FIG. 5.

Further, as illustrated in FIG. 17, the third light source 73 may have a configuration in which a light emitting element 86 is not a combination of a light emitting element 86a and the fluorescent body 86b. In this case, the light emitting element 86 is, for example, a semiconductor element such as an LED (light emitting diode) or an LD.

The light source unit 20 illustrated in FIGS. 16 and 17 irradiates, for example, white light as the illumination light Ls, and in a case where the first light source 71, the second light source 72, and the third light source 73 emit the light having different wavelengths, the light to be emitted is not particularly limited.

For example, the first light source 71 emits blue light, and the second light source 72 emits violet light, for example. The third light source 73 emits the green light including two color components in which the first color component is green and the second color component is red, with different wavelengths. A light emitting spectrum LE shown in FIG. 6 is also obtained in the light source unit 20 shown in FIGS. 16 and 17.

Even though the distance Ld between the distal end part 12d of the endoscope and the object Ob changes, the light quantity of the illumination light Ls is also controlled such that the brightness of the endoscopic image becomes constant in the light source unit 20 shown in FIGS. 16 and 17.

The control according to the control method of the above-described endoscope system can be performed in the endoscope system having the light source unit 20 shown in FIGS. 16 and 17.

With the light source unit 20 having the above-described four light sources shown in FIG. 5, the present invention is not particularly limited to obtain the light emitting spectrum LE shown in FIG. 6. For example, the light emitting spectrum LE shown in FIG. 18 is obtained by the first light source 71, the second light source 72, the third light source 73, and the fourth light source 74.

Figure 18:
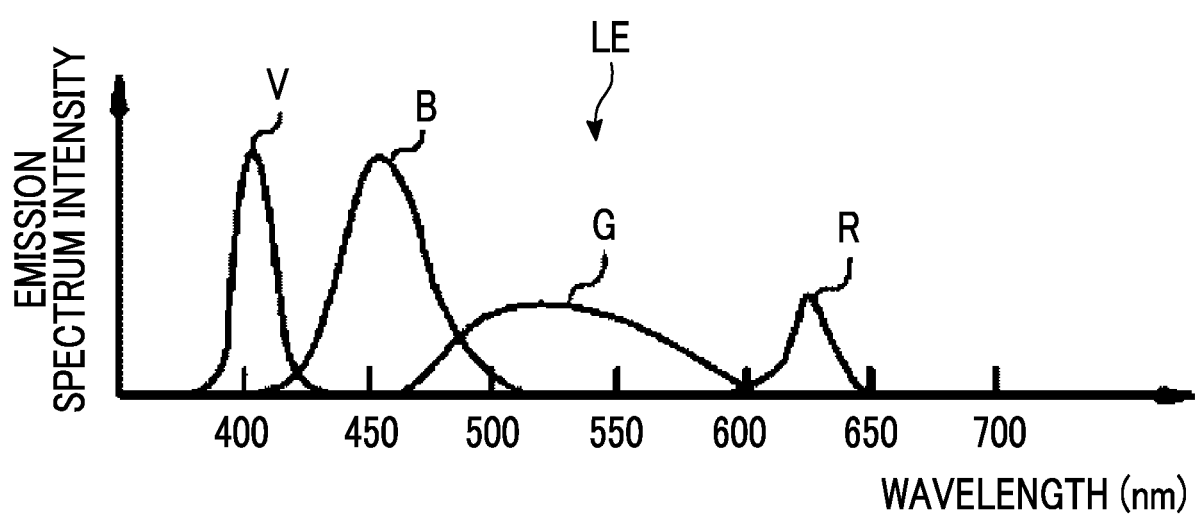
FIG. 18 is a graph illustrating another example of the light emitting spectrum of the light source unit.

FIG. 18 is a graph showing another example of the light emitting spectrum of the light source unit.

The light emitting spectrum LE illustrated in FIG. 18 includes red light R, green light G, blue light B, and violet light V. For example, the red light R has a wavelength band of 615 nm to 635 nm and a central wavelength of 620±10 nm. The green light G has, for example, a wavelength band of 500 nm to 600 nm and a central wavelength of 520±10 nm. The blue light B has, for example, a wavelength band of 440 nm to 470 nm, and a central wavelength of 455±10 nm. Also, the violet light V has, for example, a wavelength band of 395 nm to 415 nm, and a central wavelength of 405±10 nm. In this way, the white light is obtained and thus, the light emitting spectrum LE may have no specific light.

Further, in the light source unit 20 of the above-described any configurations, the first illumination light and the second illumination light may be emitted from different light sources, and the first illumination light and the second illumination light may be emitted from the same light source. That is, the first illumination light and the second illumination light may or may not have the same types of light. The first illumination light and the second illumination light may be emitted from at least one light source. Even though it is any of the above-described first illumination light and the second illumination light, the ratio of integral light quantity in the plurality of images can be kept constant over the plurality of images by the above-described control method.

In the light source unit 20 having any of the above-described configurations, for example, in a case where the distance Ld (see FIG. 5) between the distal end part 12d of the endoscope (see FIG. 5) and the object Ob (see FIG. 5) is changed as described above, the light quantity of the illumination light Ls is controlled such that the brightness of the endoscopic image becomes constant. At this time, even if the overshoot or the response delay occurs, the mutual image signal ratio among the plurality of images can be kept constant. Therefore, even in the observation image, even if the light quantity of the illumination light Ls is changed by changing the position of the distal end part 12d, it is possible to obtain an image of high image quality in which the change of the tone is suppressed.

The invention is basically configured as described above. Although the endoscope system of the invention has been described above in detail, the invention is not limited to the above-described embodiment, and various improvements and modifications may be made without departing from the scope of the invention.

EXPLANATION OF REFERENCES

10 Endoscope system
12 Endoscope
12a Insertion part
12b Operating part
12c Bending part
12d Distal end part
12e Angle knob
13a Zooming operating part
13b Mode changeover switch
14 Light source device
16 Processor device
17 Universal cord
18 Monitor
19 Console
20 Light source unit
21 Light source driving unit
22 Light source control unit
23 Measurement unit
24 Error calculation unit
30a Illumination optical system
30b Imaging optical system
41 Light guide
45 Illumination lens
46 Objective lens
47 Zoom lens
48 Image sensor
48a First element part
48b Second element part
48c Third element part
49 Pixel unit
49a First pixel
49b Second pixel
49c Third pixel
50 Filter unit
50B B color filter
50G G color filter
50R R color filter
50a First filter
50b Second filter
50c Third filter
54 Image acquisition unit
58 Noise reduction unit
59 Converting unit
60 Correction quantity calculation unit
61 Image processing unit
66 Display control unit
69 Control unit
70 Imaging control unit
71 First light source
72 Second light source
73 Third light source
74 Fourth light source
76, 77, 79 Multiplexing member
78, 82, 84 Lens
81, 83, 86, 86a, 88 Light emitting element
86b Fluorescent body
87, 89 Lens
91, 92, 93, 97 Photodetector
94, 95, 96, 98 Beam splitter
98 Beam splitter
100, 102, 104, 106, 108, 109 Light quantity waveform
100a, 102a Region
112, 114 Light absorption coefficient
B Blue light
Bf, Gf, Rf Spectral sensitivity
G Green light
LE Light emitting spectrum
Ld Distance
Lr Reflected light
Ls Illumination light
Ob Object
R Red light
$S_4$ Light about 470 nm wavelength
t Time (exposure time)
tc Time (corrected exposure time)
te Time (light emitting time in standard state)
ts Time (time to close corrected electronic shutter)
V Violet light

What is claimed is:

1. An endoscope system comprising:
   a plurality of light sources which emits light having different wavelengths;
   a photodetector which is provided in each of the plurality of light sources, and which receives a part of light from the plurality of light sources and obtains information on a light emitting quantity of the plurality of light sources;
   a digital signal processor which acquires an image to be observed for each of a plurality of illumination lights comprising at least first illumination light and second illumination light composed of light emitted from at least one of the plurality of light sources; and
   a processor which makes a ratio of a R pixel value, a G pixel value, and a B pixel value of each of the plurality of images acquired by the digital signal processor be the same as one another,
   wherein the processor changes a light emitting quantity of the light source according to a light receiving quantity of the photodetector such that the light emitting quantity of the light source meets a target light quantity,
   wherein the processor further comprises:
   obtaining a first integrated light quantity obtained using the photodetector in a predetermined error calculation period after turning on the light source; and
   obtaining a difference between the first integrated light quantity and the target light quantity, and
   wherein the processor changes the target light quantity after the error calculation period according to the difference to make a second integrated light quantity constant in a predetermined exposure period.

2. The endoscope system according to claim 1, wherein the first illumination light and the second illumination light are emitted from different light sources.

3. The endoscope system according to claim 2, wherein the processor changes a timing of turning off the light source after the error calculation period according to the difference to make the second integrated light quantity constant in the predetermined exposure period.

4. The endoscope system according to claim 2, wherein the processor changes the predetermined exposure period according to the difference to make the second integrated light quantity constant in the exposure period.

5. The endoscope system according to claim 2, wherein the processor changes the target light quantity of the second illumination light according to the difference in the first illumination light to make a ratio of integrated light quantities constant in the predetermined exposure period in the plurality of images.

6. The endoscope system according to claim 2, wherein the processor changes a timing of turning off the second illumination light according to the difference in the first illumination light to make a ratio of integrated light quantities constant in the predetermined exposure period in the plurality of images.

7. The endoscope system according to claim 1, wherein the first illumination light and the second illumination light are emitted from the same light source.

8. The endoscope system according to claim 7, wherein the processor changes a timing of turning off the light source after the error calculation period according to the difference to make the second integrated light quantity constant in the predetermined exposure period.

9. The endoscope system according to claim 7, wherein the processor changes the predetermined exposure period according to the difference to make the second integrated light quantity constant in the exposure period.

10. The endoscope system according to claim 7, wherein the processor changes the target light quantity of the second illumination light according to the difference in the first illumination light to make a ratio of integrated light quantities constant in the predetermined exposure period in the plurality of images.

11. The endoscope system according to claim 7, wherein the processor changes a timing of turning off the second illumination light according to the difference in the first illumination light to make a ratio of integrated light quantities constant in the predetermined exposure period in the plurality of images.

12. The endoscope system according to claim 1, wherein the processor changes a timing of turning off the light source after the error calculation period according to the difference to make the second integrated light quantity constant in the predetermined exposure period.

13. The endoscope system according to claim 1, wherein the processor changes the predetermined exposure period according to the difference to make the second integrated light quantity constant in the exposure period.

14. The endoscope system according to claim 1, wherein the processor changes the target light quantity of the second illumination light according to the difference in the first illumination light to make a ratio of integrated light quantities constant in the predetermined exposure period in the plurality of images.

15. The endoscope system according to claim 1, wherein the processor changes a timing of turning off the second illumination light according to the difference in the first illumination light to make a ratio of integrated light quantities constant in the predetermined exposure period in the plurality of images.

16. The endoscope system according to claim 1, wherein the processor changes an exposure period of the second illumination light according to the difference in the first illumination light to make a ratio of integrated light quantities constant in the predetermined exposure period in the plurality of images.

17. The endoscope system according to claim 1, wherein the plurality of light sources has a laser diode or a light emitting diode.

18. The endoscope system according to claim 1, wherein the photodetector is a photodiode.

* * * * *